(12) United States Patent
Kenyon

(10) Patent No.: US 11,846,303 B2
(45) Date of Patent: Dec. 19, 2023

(54) IMPELLER WITH INCLINED AND REVERSE INCLINED BLADES

(71) Applicant: ResMed Pty Ltd, Bella Vista (AU)

(72) Inventor: Barton John Kenyon, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 389 days.

(21) Appl. No.: 17/091,461

(22) Filed: Nov. 6, 2020

(65) Prior Publication Data

US 2021/0262490 A1 Aug. 26, 2021

Related U.S. Application Data

(63) Continuation of application No. 15/736,175, filed as application No. PCT/AU2016/050508 on Jun. 16, 2016, now Pat. No. 10,844,876.

(Continued)

(51) Int. Cl.
*F04D 29/66* (2006.01)
*A61M 16/00* (2006.01)
(Continued)

(52) U.S. Cl.
CPC ....... *F04D 29/666* (2013.01); *A61M 16/0066* (2013.01); *A61M 16/022* (2017.08); *F04D 29/023* (2013.01); *F04D 29/281* (2013.01); *F04D 29/30* (2013.01); *F04D 29/667* (2013.01); *A61M 16/06* (2013.01); *A61M 16/0633* (2014.02); *A61M 16/0683* (2013.01);
(Continued)

(58) Field of Classification Search
CPC ...... F04D 29/666; F04D 29/023; F04D 29/66; F04D 29/30; F04D 29/281; A61M 2016/0027; A61M 2016/0039; A61M 2207/00; A61M 2205/42; F05D 2240/304; F05D 2250/75
See application file for complete search history.

(56) References Cited

U.S. PATENT DOCUMENTS 1,561,847 A 11/1925 Green
2,540,136 A * 2/1951 Oliphant ............... F04D 29/281
415/206

(Continued)

FOREIGN PATENT DOCUMENTS

DE 8518403 8/1985
EP 0942175 11/2004
(Continued)

OTHER PUBLICATIONS

International Search Report for PCT/AU2016/050508, dated Aug. 23, 2016, 5 pages.

(Continued)

*Primary Examiner* — Bradley H Philips
*Assistant Examiner* — Savannah L Gabriel
(74) *Attorney, Agent, or Firm* — Nixon & Vanderhye P.C.

(57) ABSTRACT

An impeller for use in a centrifugal blower, the impeller includes a hub defining an axis of rotation for the impeller; a plurality of inclined blades, the plurality of inclined blades extending away from the hub; and a plurality of reverse inclined blades, the plurality of reverse inclined blades extending away from the hub. Each of the plurality of inclined blades are joined to an adjacent inclined blade at least in part by a reverse inclined blade.

31 Claims, 21 Drawing Sheets

Related U.S. Application Data

(60) Provisional application No. 62/180,279, filed on Jun. 16, 2015.

(51) Int. Cl.
| | | |
|---|---|---|
| *F04D 29/28* | (2006.01) | |
| *F04D 29/30* | (2006.01) | |
| *F04D 29/02* | (2006.01) | |
| *A61M 16/06* | (2006.01) | |

(52) U.S. Cl.
CPC ........... *A61M 2016/0027* (2013.01); *A61M 2016/0039* (2013.01); *A61M 2205/42* (2013.01); *A61M 2207/00* (2013.01); *F05D 2240/304* (2013.01); *F05D 2250/75* (2013.01)

(56) References Cited

U.S. PATENT DOCUMENTS

| | | | | |
|---|---|---|---|---|
| 3,746,467 | A * | 7/1973 | Buse | F04D 29/2288 |
| | | | | 416/228 |
| 4,364,712 | A * | 12/1982 | Charles | F04D 29/326 |
| | | | | 416/189 |
| 4,717,408 | A * | 1/1988 | Hopewell | F25J 3/0238 |
| | | | | 62/633 |
| 4,782,832 | A | 11/1988 | Trimble et al. | |
| 4,944,310 | A | 7/1990 | Sullivan | |
| 6,532,959 | B1 | 3/2003 | Berthon-Jones | |
| 6,581,594 | B1 | 6/2003 | Drew et al. | |
| 7,455,504 | B2 * | 11/2008 | Hill | F04D 17/167 |
| | | | | 416/179 |
| 7,866,944 | B2 | 1/2011 | Kenyon et al. | |
| 8,393,320 | B2 | 3/2013 | Kenyon | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 10,124,135 | B2 * | 11/2018 | Kenyon | F04D 29/444 |
| 10,844,876 | B2 | 11/2020 | Kenyon | |
| 2004/0258527 | A1 | 12/2004 | Kaneko et al. | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2011/0023874 | A1 | 2/2011 | Bath et al. | |
| 2012/0244008 | A1 * | 9/2012 | Chang | F04D 29/666 |
| | | | | 416/244 R |
| 2012/0263599 | A1 | 10/2012 | Sugimura | |
| 2014/0227091 | A1 | 8/2014 | Kenyon et al. | |
| 2015/0030441 | A1 | 1/2015 | Wu et al. | |
| 2015/0128942 | A1 | 5/2015 | Tatkov et al. | |
| 2015/0152875 | A1 * | 6/2015 | Kamiya | F04D 29/681 |
| | | | | 416/147 |
| 2017/0058911 | A1 * | 3/2017 | Baryshnikov | F04D 29/043 |
| 2018/0180062 | A1 | 6/2018 | Kenyon | |

FOREIGN PATENT DOCUMENTS

| | | |
|---|---|---|
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |

OTHER PUBLICATIONS

Written Opinion of the ISA for PCT/AU2016/050508, dated Aug. 23, 2016, 4 pages.

International Prelimimary Report on Patentability with Amended Sheets, dated May 30, 2017, 27 pages.

"Respiratory Physiology", by John B. West, Lippincott Williams & Wilkins, 9th edition published 2012 (8 pages).

Supplementary European Search Report for EP Application No. 16810628.4, dated Jan. 21, 2019, 7 pages.

Kenyon, Barton John, U.S. Appl. No. 15/736,175, filed Dec. 13, 2017, for "Impeller With Inclined and Reverse Inclined Blades," (parent application).

* cited by examiner

IMPELLER WITH INCLINED AND REVERSE INCLINED BLADES

This application is a continuation of U.S. application Ser. No. 15/736,175, filed Dec. 13, 2017, which is the U.S. national phase of International Application No. PCT/AU2016/050508, filed Jun. 16, 2016, which designated the U.S. and claims the benefit of U.S. Provisional Patent Application No. 62/180,279, filed Jun. 16, 2015, the entire contents of each of which are incorporated herein by reference.

1 BACKGROUND OF THE TECHNOLOGY

1.1 Field of the Technology

The present technology relates to an impeller for a blower. More specifically, the present technology relates to an impeller for a blower suitable for medical devices or apparatus, such as for respiratory pressure therapy, and its use. The medical device or apparatus may relate to one or more of the detection, diagnosis, treatment, prevention and amelioration of respiratory-related disorders.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

1.2.2 Therapy

Various therapies, such as Continuous Positive Airway Pressure (CPAP) therapy, Non-invasive ventilation (MV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory insufficiency, in forms such as OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

1.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

Table of noise output levels of prior RPT devices (one specimen only, measured using test method specified in ISO 3744 in CPAP mode at 10 cm H₂O).

| RPT Device name | A-weighted sound power level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or pediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.2.1 Impeller

Many RPT devices comprise a blower configured to receive a flow of gases (e.g. air) and increase its pressure and/or velocity in order to generate a pressurised flow of gases. A blower may comprise one or more impellers, such as centrifugal, axial and mixed flow impellers.

A blower for an RPT device typically operates to provide a flow of air at a flow rate of up to 200 L/min, such as between 20 and 150 L/min, or between 30 and 120 L/min. The blower may provide the flow of air at a pressure of up to 50 cm H₂O, such as between 2 and 40 cm H₂O or 3 and 30 cm H₂O. A blower may comprise one or more impellers, such as one, two, three or four impellers.

A blower for an RPT device, and hence an impeller used therein, preferably operates effectively and quietly over a wide range of flow rates, including zero and reverse flows (i.e. wherein the air flows in a reverse direction to its intended operating direction). For example, if therapy pressure is low (which likely results in a low leak flow and/or low vent flow) and the patient's breathing volume is high, the flow rate in the blower might change from approximately +70 to −30 l/min during the breath cycle. Throughout this cycle, preferably, the blower must remain quiet, such as to not disturb the user. In another example, if therapy pressure is high and leak is high, but patient breathing volume remains high, the flow rate might instead change from +150 to +50 l/min. This dynamic flow situation makes an RPT application quite different from, for example, an air conditioning application, or a jet engine, where operation is in a narrow zone around a particular design flow.

An impeller for an RPT device may rotate at speeds of up to 60,000 rpm, such as up to 50,000 rpm. In comparison, a large jet engine for example may rotate at 10,000 rpm, or a turbine in an automotive turbocharger may operate at speeds of up to 150,000 rpm. However, the aerodynamic flow regime is very different from either of the above types, at least in part due to a relatively small diameter of impellers in an RPT device.

For example, air flow in an automotive turbocharger can approach and/or exceed the speed of sound, thus creating transonic and/or supersonic flow (i.e. Mach numbers approaching or exceeding 1) and causing the air flow to behave as 'compressible flow'. An exemplary impeller for an RPT device rotating at speeds up to 60,000 rpm with a diameter of 30 mm moves at a tip speed of up to 94 m/s, or Mach 0.27. Such air flow can be substantially characterised as 'incompressible flow'.

Thus, while rotating at relatively high angular speeds, the aerodynamic behaviour of an impeller in an RPT device is very different to those previously described, such as a turbocharger. This discrepancy leads therefore to a very different set of requirements from an aerodynamic perspective.

Desired characteristics of blowers for RPT devices include cost-effectiveness, quietness and efficiency. Impellers used in other fields may have different requirements altogether.

For example, noise requirements for an impeller for an RPT device may differ by orders of magnitudes to impellers in other fields such as turbo-machinery. As described above, RPT devices are often used in quiet bedrooms where the background noise level may be approximately 30 dB(A) (sound pressure level). On the other hand, an automotive turbocharger may be installed in an engine bay of a motor vehicle, for which a noise level in the cabin may exceed 60 dB(A). Turbo-machinery used in industrial settings may similarly have a very different noise requirement to that an RPT device.

A centrifugal impeller for an RPT device may also preferably comprise a low rotational inertia to readily allow acceleration and deceleration. For example, an impeller for an RPT device may need to provide different pressures according to a portion of a patient's respiratory cycle.

Similarly, cost requirements for a component (e.g. an impeller) of an RPT device may be very different to that of an industrial, aeronautical or automotive impeller.

Prior art impellers, even those used in RPT devices, may for example perform well to meet some of the desired characteristics, however not in others.

In one example, a centrifugal impeller comprising one or more disc-like shrouds and perpendicular blades may perform efficiently, and may be produced at a low-cost using injection moulding, as the impeller is in a 'line of draw'. However, such a manufacturing technique does not easily allow for an impeller blade to be inclined.

On the other hand, centrifugal impellers comprising an inclined blade and a disc-like shroud may provide an improved noise characteristic in some respects (e.g. by skewing pressure pulses, as will be described in further detail below). Such a centrifugal impeller however may be difficult to produce with injection moulding process, an alternative process to which may subsequently increase costs.

For example, a centrifugal impeller comprising inclined blades may be machined, for example from a metal billet. However, a machining process may be significantly more costly in comparison to an injection moulding process. Furthermore, it may result in an impeller with a higher than desired rotational inertia due to the higher density of the metal used (e.g. aluminium) in comparison to an injection moulded polymer (e.g. polycarbonate).

In a yet further alternative, centrifugal impellers may comprise inclined blades that are unsupported. That is, these impellers may substantially not comprise a shroud. Thus, these centrifugal impellers may comprise inclined blades and may be produced using injection moulding. However, such an impeller may not be suitable for high-speed applications (e.g. rotation at 50,000 rpm) due to a low rigidity of the impeller, particularly in the rotational direction.

For at least the above reasons, a blower and/or an impeller for an RPT device may comprise a unique set of requirements and/or constraints to its designer(s).

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

2 BRIEF SUMMARY OF THE TECHNOLOGY

The present technology may be directed towards providing a blower for producing a flow of fluids, such as breathable gases. The present technology may be directed towards an impeller for a blower, having one or more of improved cost, performance, and manufacturability. More specifically, the blower may be directed towards use in a respiratory therapy device.

Some forms of the present technology are directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology comprises impeller for use in a centrifugal blower, the impeller comprising: a hub defining an axis of rotation for the impeller; a plurality of inclined blades, the plurality of inclined blades extending away from the hub; and a plurality of reverse inclined blades, the plurality of reverse inclined blades extending away from the hub, wherein each of the plurality of inclined blades are joined to an adjacent inclined blade at least in part by a reverse inclined blade.

In examples, (a) each of the plurality of inclined blades forms a substantially V-shaped cross-section with the adjacent reverse inclined blade; (b) the plurality of inclined blades and the plurality of reverse inclined blades are connected together in a continuous manner at a circumference of the impeller that is radially outward from the hub; (d) the impeller further comprises a plurality of flat sectors that are each substantially perpendicular to the axis of rotation, wherein a portion of the sectors are at the circumference; (e) the flow path extends to the outer perimeter; (f) the plurality of inclined blades and the plurality of reverse inclined blades are formed without an undercut; (g) the impeller is formed by injection moulding with all features of the impeller being formed along a line of draw of the injection moulding; (h) the line of draw is substantially parallel to the axis of rotation; (i) the plurality of inclined blades are inclined at a positive angle with the axis of rotation, the positive angle being neither parallel nor perpendicular; the plurality of reverse inclined blades are inclined at a negative angle with the axis of rotation; and the positive angle and the negative angle have the same absolute value; (j) the plurality of inclined blades are inclined at a first constant angle along the entire radial length of the plurality of inclined blades, and the plurality of reverse inclined blades are inclined at a second constant angle along the entire radial length of the plurality of reverse inclined blades; (k) the plurality of inclined blades are inclined at a first angle that varies along a radial length of the plurality of inclined blades, and the plurality of reverse inclined blades are inclined at a second angle that varies along a radial length of the plurality of reverse inclined blades; (l) tips of the plurality of inclined blades are configured such that pressure pulses coming off of tips of the plurality of inclined blades are skewed to reduce noise; (m) the plurality of inclined blades and the plurality of reverse inclined blades define primary air passages on a first face of the impeller and secondary air passages on a second face of the impeller; (n) the impeller further comprising a plurality of openings configured to allow air to flow from the second face and radially outward through the primary passages; (o) the plurality of inclined blades extend to the hub and the plurality of reverse inclined blades do not extend to the hub; (p) the plurality of inclined blades do not extend to the hub and the plurality of reverse inclined blades extend to the hub; (q) the plurality of inclined blades and the plurality of reverse inclined blades extend to the hub and the plurality of openings are through a portion of the plurality of inclined blades and/or the plurality of reverse inclined blades; (r) at least one of the plurality of inclined blades and the plurality of reverse inclined blades includes serrations on at least one of a respective trailing edge and a respective leading edge; (s) a blade tip of at least one of the plurality of inclined blades and the plurality of reverse inclined blades includes serrations; and/or (t) a respiratory pressure therapy device for generating a supply of air at positive pressure for the amelioration or treatment of a respiratory disorder, the respiratory pressure therapy device comprising: a controller configured to control the respiratory therapy device to provide flow rates and pressures suitable for respiratory therapy; and a pressure generator including the impeller, a housing for the impeller and an electric motor configured to rotate the impeller.

One form of the present technology comprises an impeller for generating a supply of air at positive pressure for the amelioration or treatment of a respiratory disorder, the impeller comprising: a hub defining an axis of rotation for the impeller; a plurality of inclined blades each including a rotationally rearward edge, the plurality of inclined blades being attached to the hub; and a plurality of reverse inclined blades each including a rotationally forward edge, the plurality of reverse inclined blades being attached to the hub, wherein the plurality of inclined blades and the plurality of reverse inclined blades form a plurality of pairs of blades with the rotationally rearward edge and the rotationally forward edge connected together in a continuous manner.

In examples, (a) the rotationally rearward edge and the rotationally forward edge are connected together to form a substantially V-shaped cross-section; (b) the plurality of inclined blades each include a second rotationally forward edge, the plurality of reverse inclined blades each include a second rotationally rearward edge, and each of the second rotationally forward edges is connected to one of the second rotationally rearward edges in a continuous manner; (c) each of the second rotationally forward edges is connected to one of the second rotationally rearward edges by a flat sector that is substantially perpendicular to the axis of rotation; (d) each of the plurality of inclined blades and each of the plurality of reverse inclined blades provide a flow path in a direction from the hub towards an outer perimeter of the impeller; (e) the flow path extends to the outer perimeter; (f) the plurality of inclined blades and the plurality of reverse inclined blades are formed without an undercut; (g) the impeller is formed by injection moulding with all features of the impeller being formed along a line of draw of the injection moulding; (h) the line of draw is substantially parallel to the axis of rotation; (i) the plurality of inclined blades are inclined at a positive angle with the axis of rotation, the positive angle being neither parallel nor perpendicular; the plurality of reverse inclined blades are inclined at a negative angle with the axis of rotation; and the positive angle and the negative angle have the same absolute value; (j) the plurality of inclined blades are inclined at a first constant angle along the entire radial length of the plurality of inclined blades, and the plurality of reverse inclined blades are inclined at a second constant angle along the entire radial length of the plurality of reverse inclined blades; (k) the plurality of inclined blades are inclined at a first angle that varies along a radial length of the plurality of inclined blades, and the plurality of reverse inclined blades are inclined at a second angle that varies along a radial length of the plurality of reverse inclined blades; (l) tips of the plurality of inclined blades are configured such that pressure pulses coming off of tips of the plurality of inclined blades are skewed to reduce noise; (m) adjacent pairs of the plurality of pairs of blades define primary air passages on a first face of the impeller and the plurality of pairs of blades define secondary air passages on a second face of the impeller; (n) the impeller further comprises a plurality of openings configured to allow air to flow from the second face and radially outward through the primary passages; (o) the plurality of inclined blades extend to the hub and the plurality of reverse inclined blades do not extend to the hub; (p) the plurality of inclined blades do not extend to the hub and the plurality of reverse inclined blades extend to the hub; (q) the plurality of inclined blades and the plurality of reverse inclined blades extend to the hub and the plurality of openings are through a portion of the plurality of inclined blades and/or the plurality of reverse inclined blades; (r) at least one of the plurality of inclined blades and the plurality of reverse inclined blades includes serrations on at least one of a respective rotationally rearward edge and a respective rotationally forward edge; (s) a blade tip of at least one of the plurality of inclined blades and the plurality of reverse inclined blades includes serrations; and/or (t) a respiratory pressure therapy device for generating a supply of air at positive pressure for the amelioration or treatment of a respiratory disorder, the respiratory pressure therapy device comprising: a controller configured to control the respiratory therapy device to provide flow rates and pressures suitable for respiratory therapy; and a pressure generator including the impeller a housing for the impeller and an electric motor configured to rotate the impeller.

An aspect of one form of the present technology is a method of manufacturing the apparatus described above.

An aspect of certain forms of the present technology is a medical device that is easy to use, e.g. by a person who does not have medical training, by a person who has limited dexterity or by a person with limited experience in using this type of medical device.

An aspect of one form of the present technology is a portable RPT device that may be carried by a person, e.g., around the home of the person.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1 shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

3.2 Patient Interface

FIG. 2 shows a patient interface in the form of a nasal mask in accordance with one form of the present technology.

3.3 RPT Device

3.4 Humidifier

Figure 1:
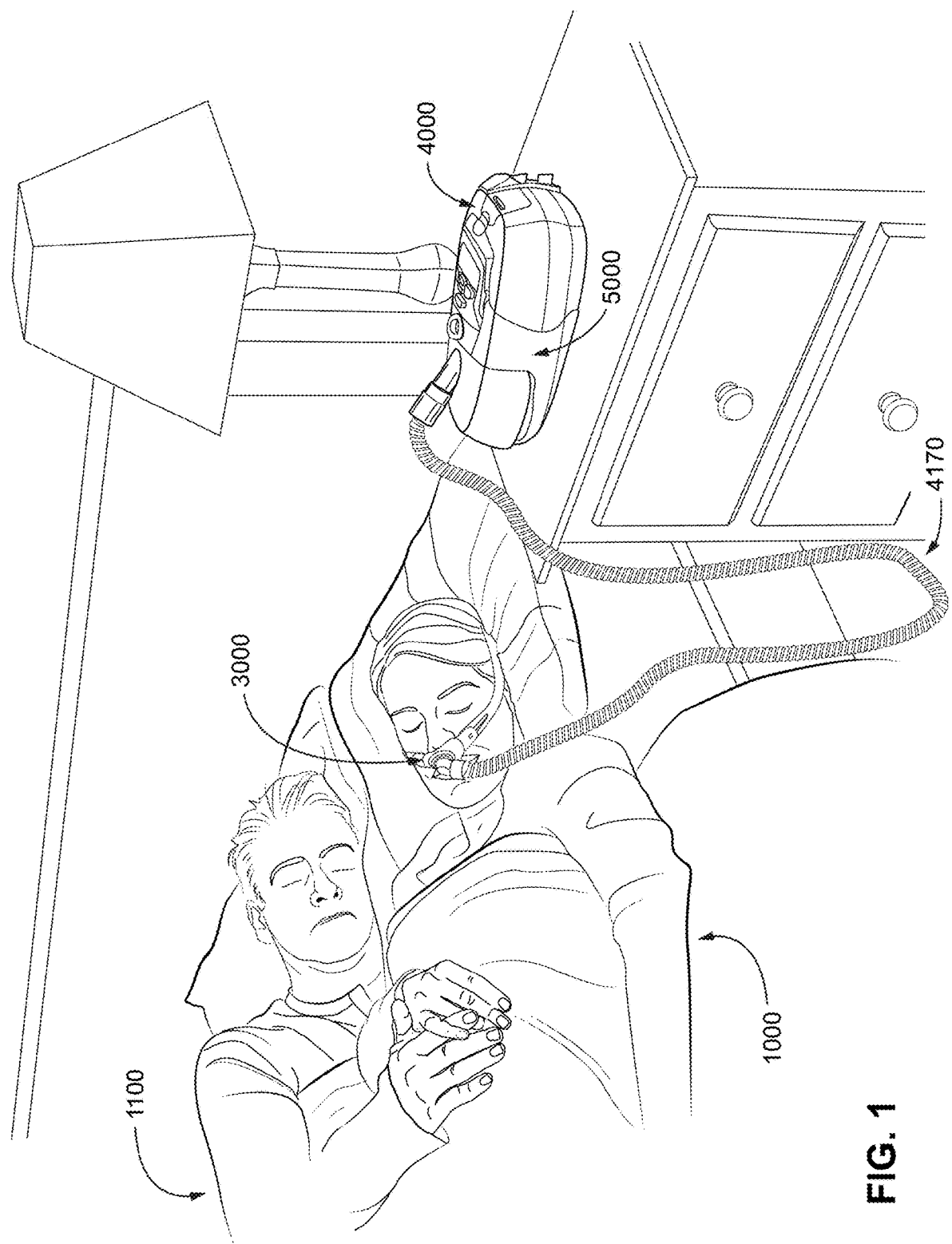
Figure 2:
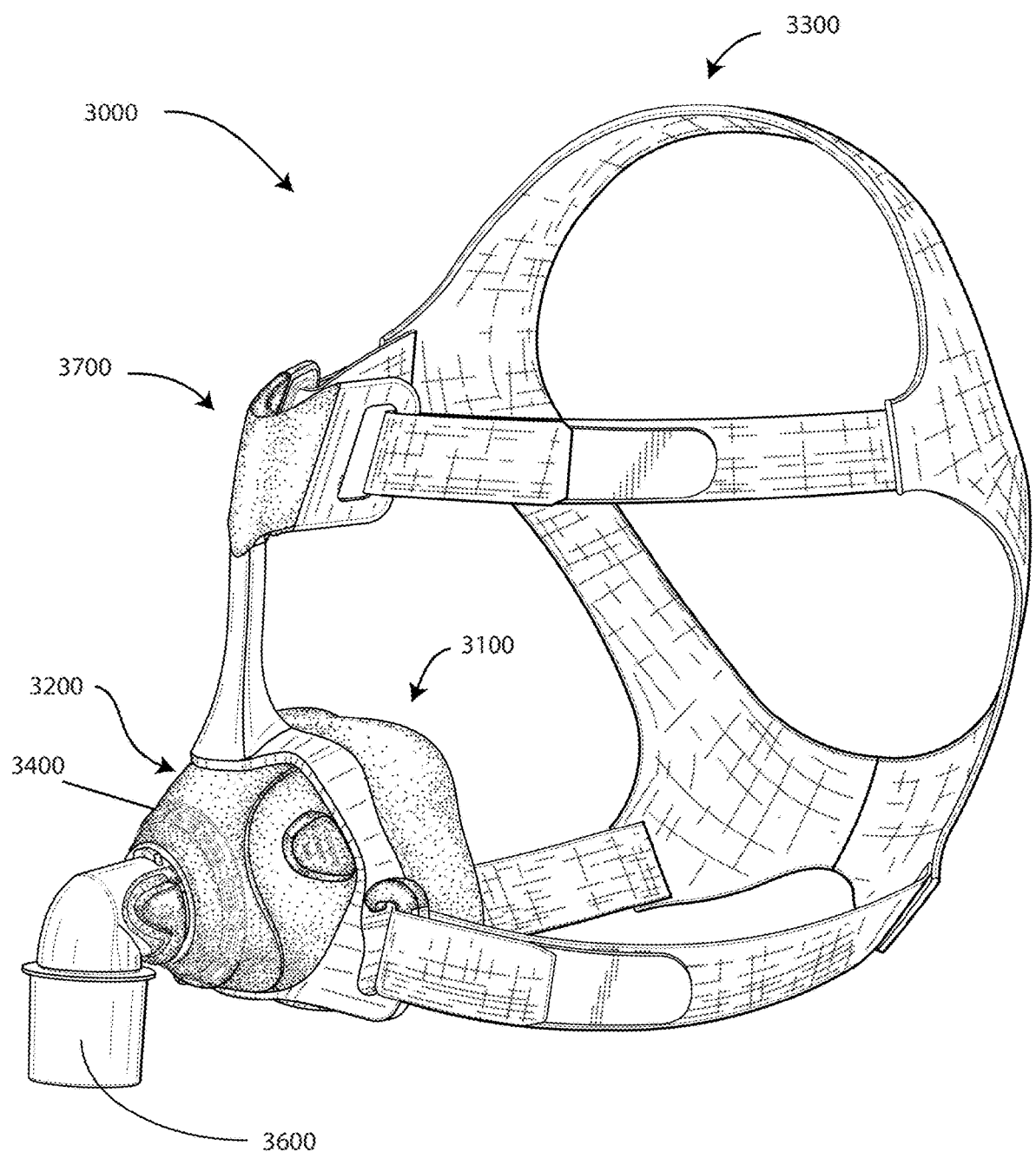
Figure 3A:
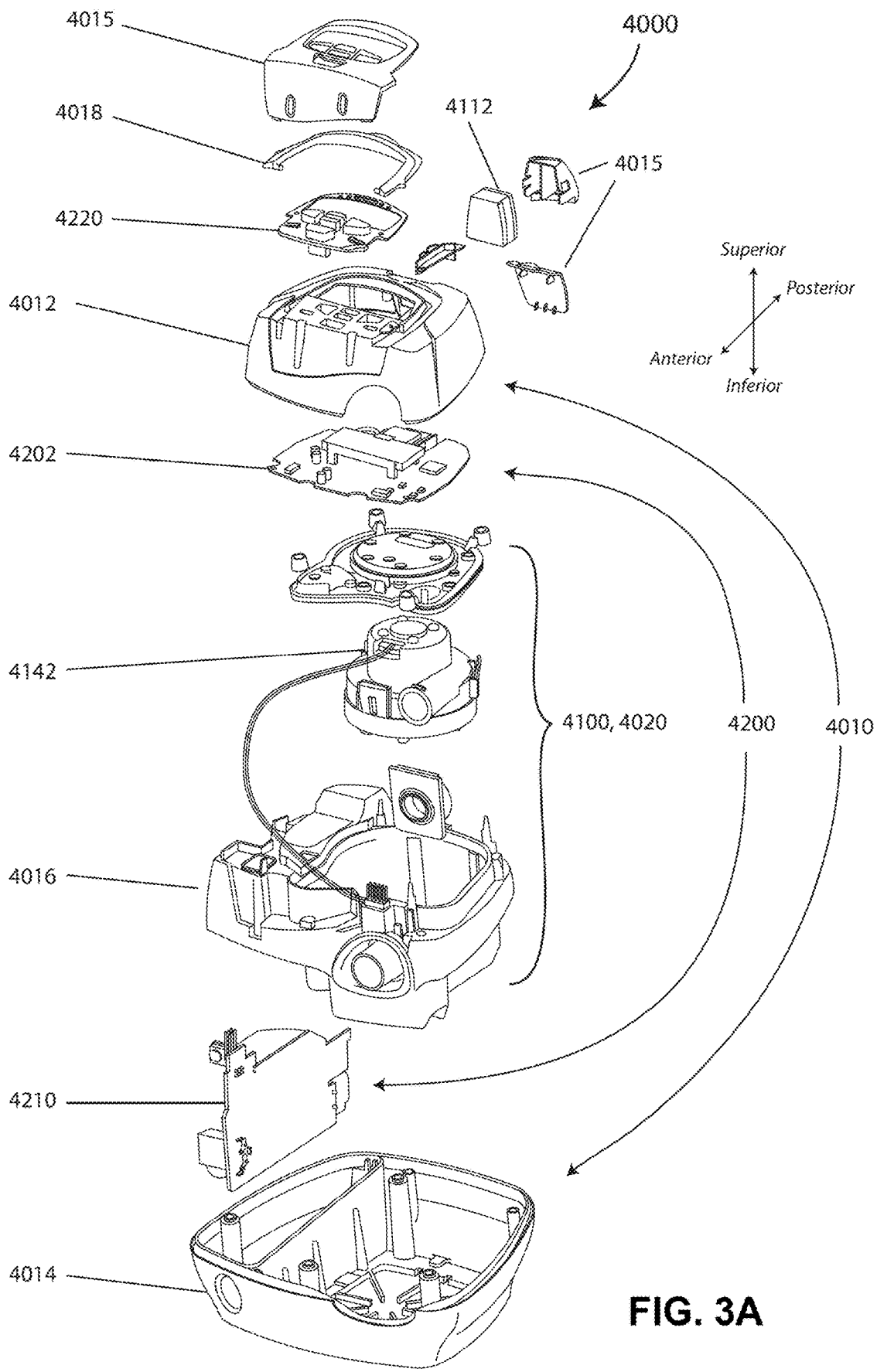
FIG. 3A shows an RPT device in accordance with one form of the present technology.
Figure 3B:
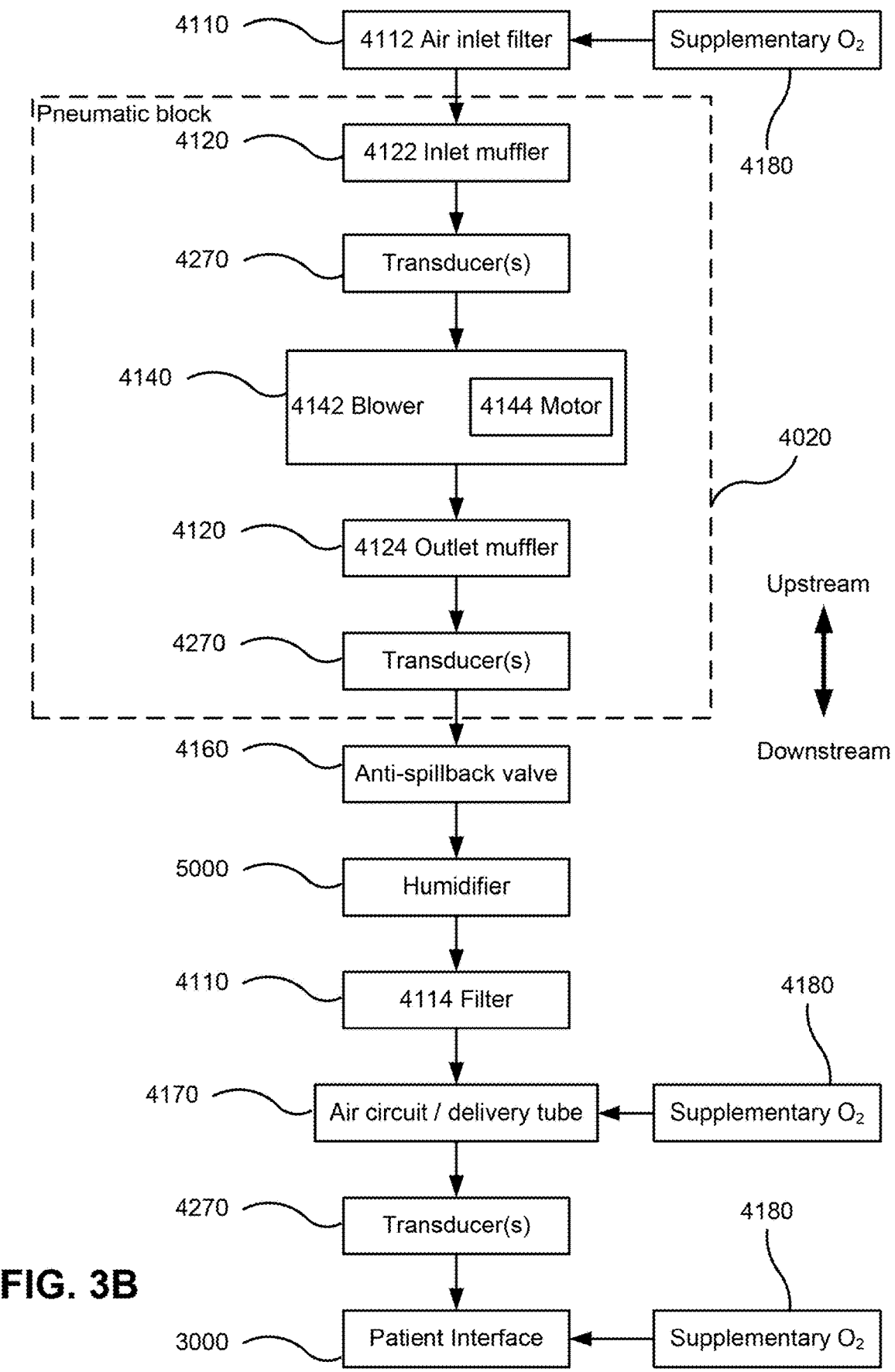
FIG. 3B is a schematic diagram of the pneumatic path of an RPT device in accordance with one form of the present technology. The directions of upstream and downstream are indicated.
Figure 4A:
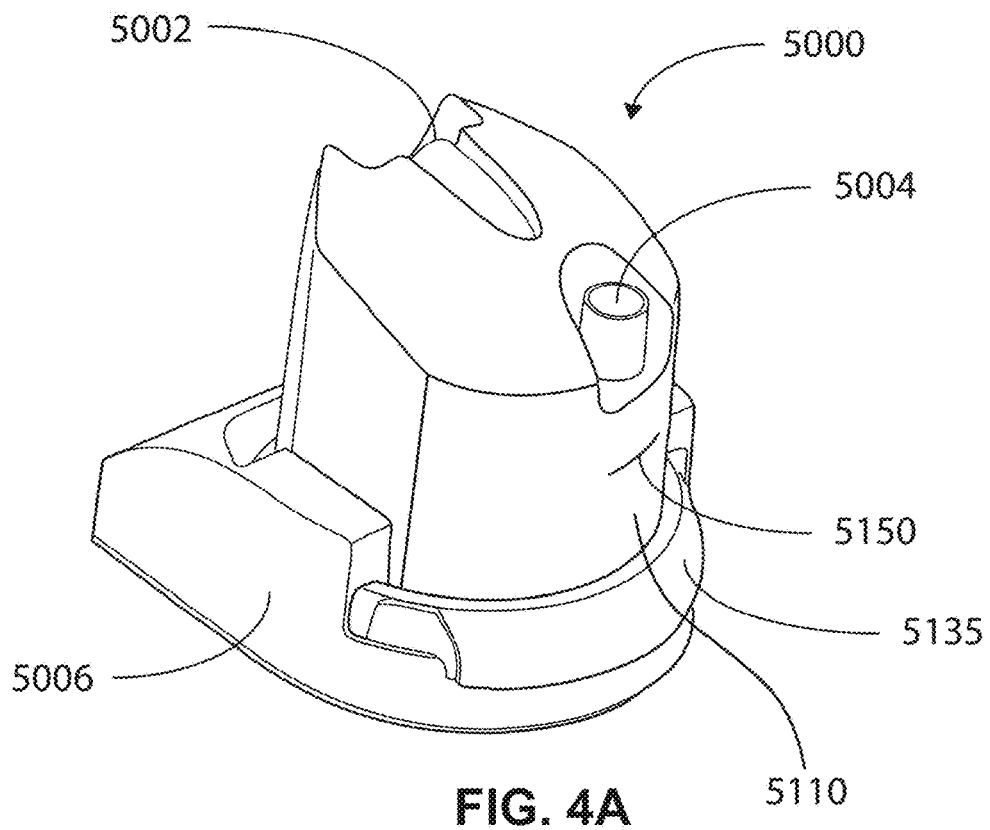

FIG. 4A shows an isometric view of a humidifier in accordance with one form of the present technology.

Figure 4B:
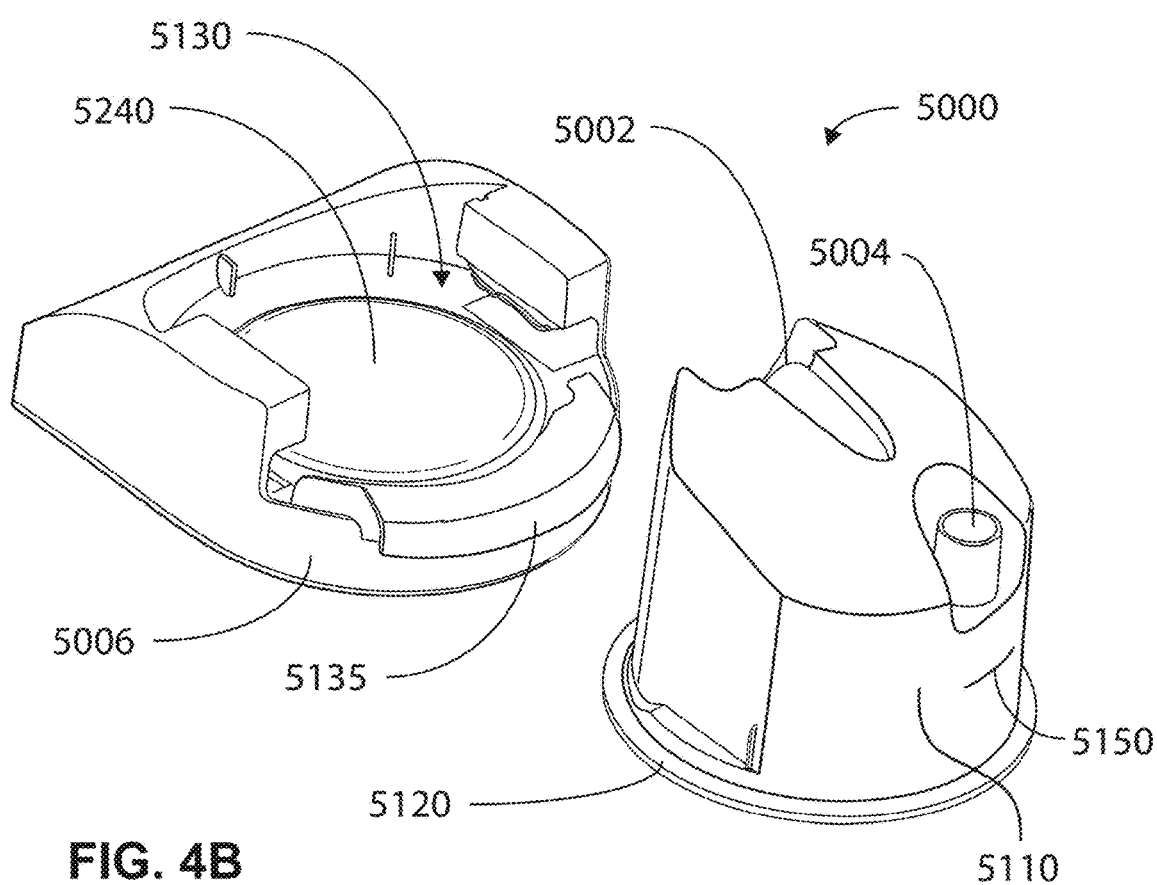

FIG. 4B shows an isometric view of a humidifier in accordance with one form of the present technology, showing a humidifier reservoir 5110 removed from the humidifier reservoir dock 5130.

3.5 Breathing Waveforms

Figure 5:
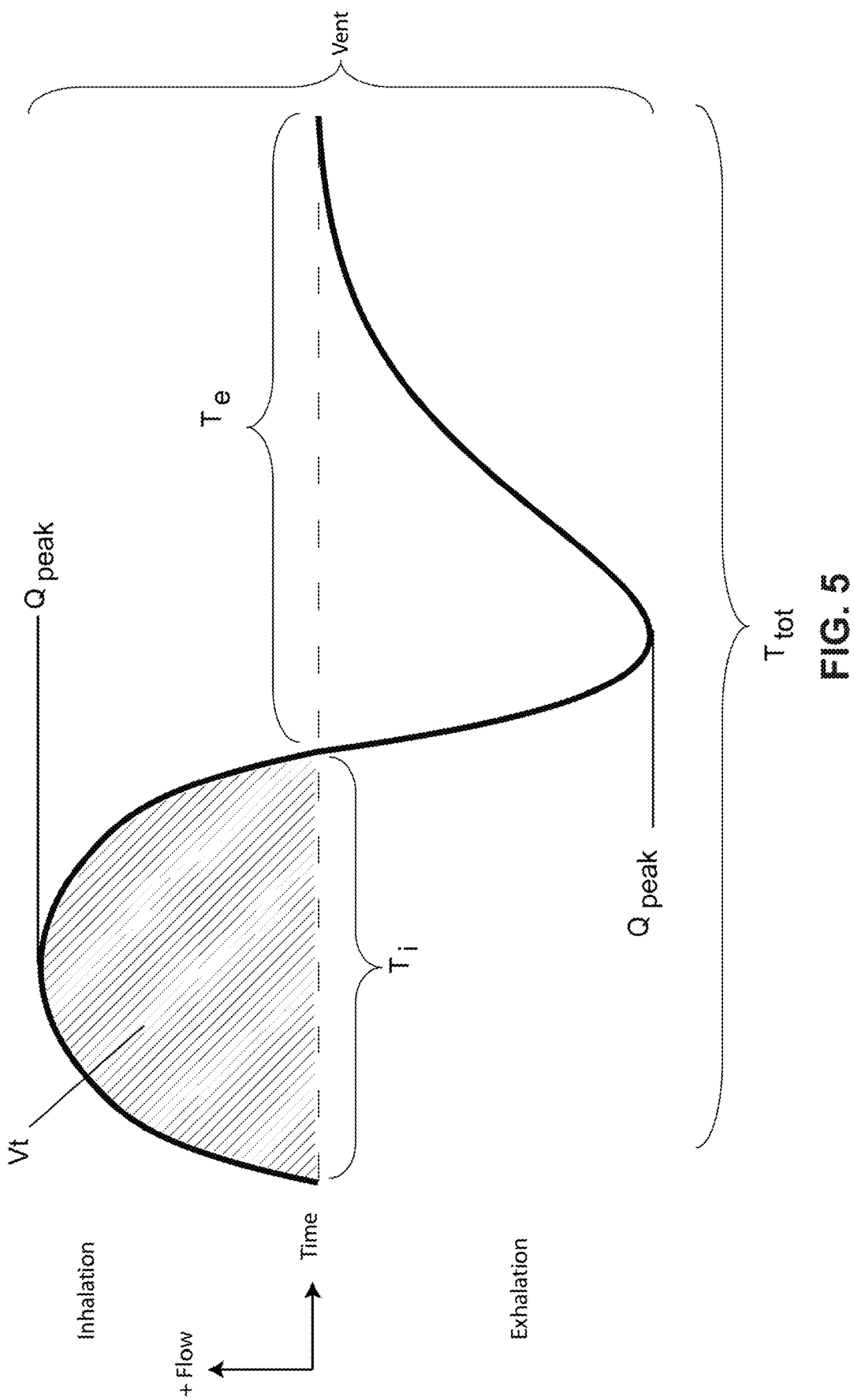

FIG. 5 shows a model typical breath waveform of a person while sleeping.

3.6 Impeller

Figure 6A:
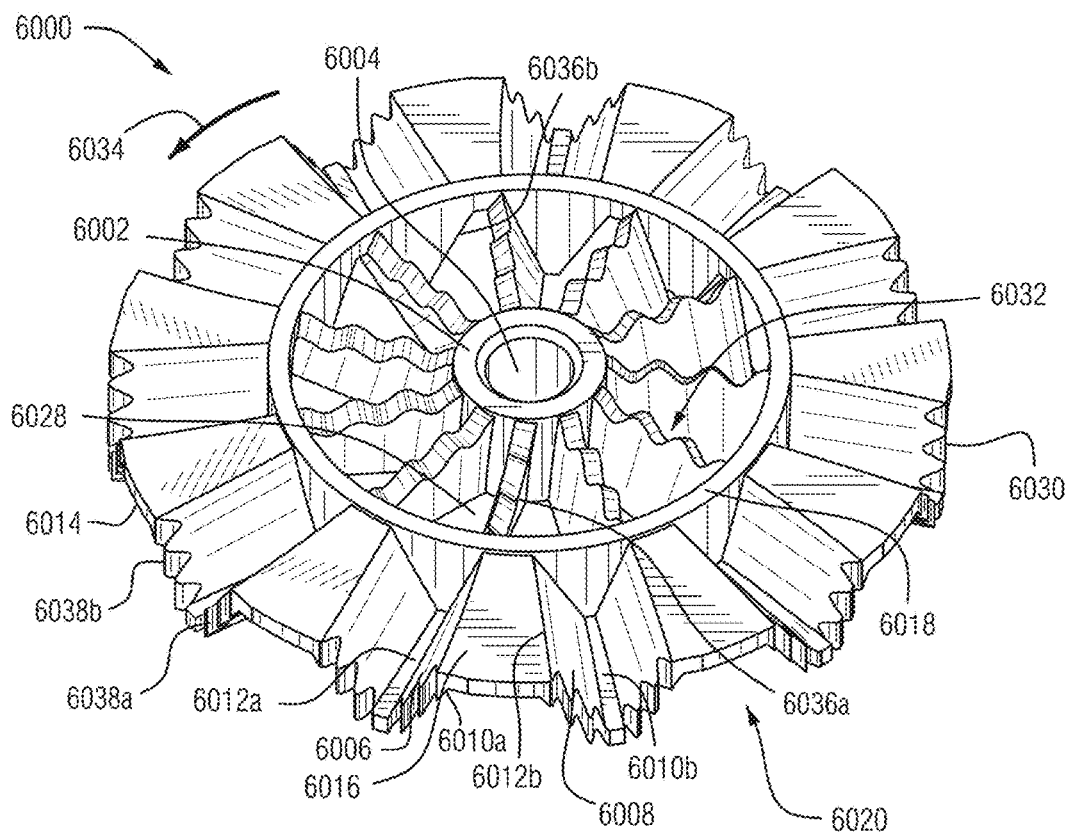

FIG. 6A shows a perspective view of an impeller suitable for use with a blower in an RPT device.

Figure 6B:
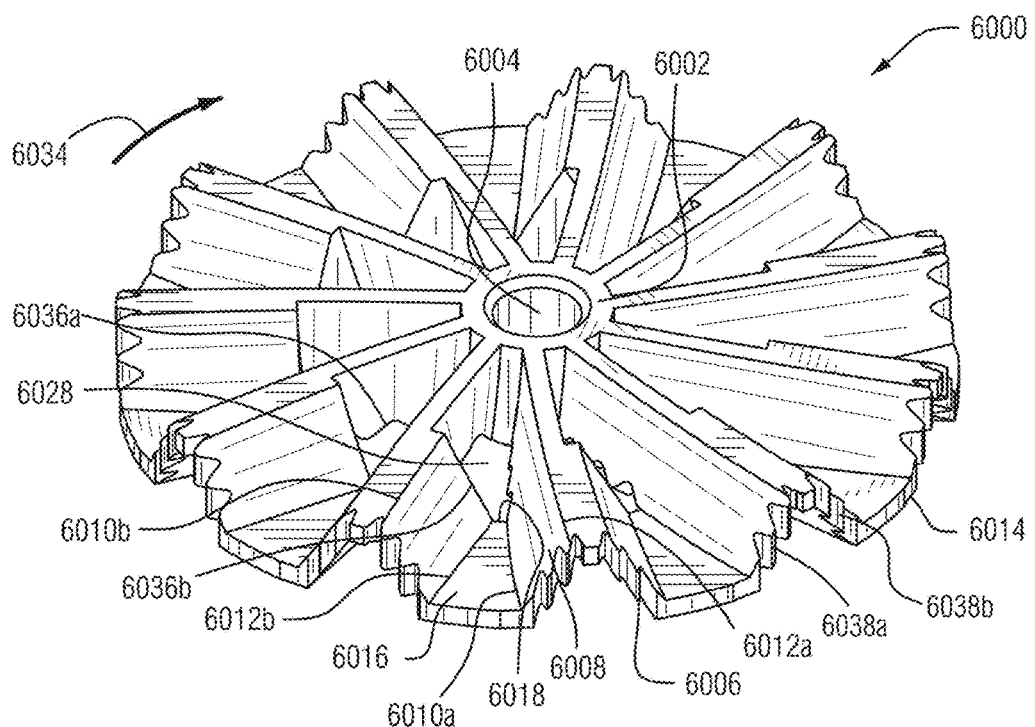

FIG. 6B shows another perspective view of the impeller viewed from an opposite side from that illustrated in FIG. 6A.

Figure 6C:
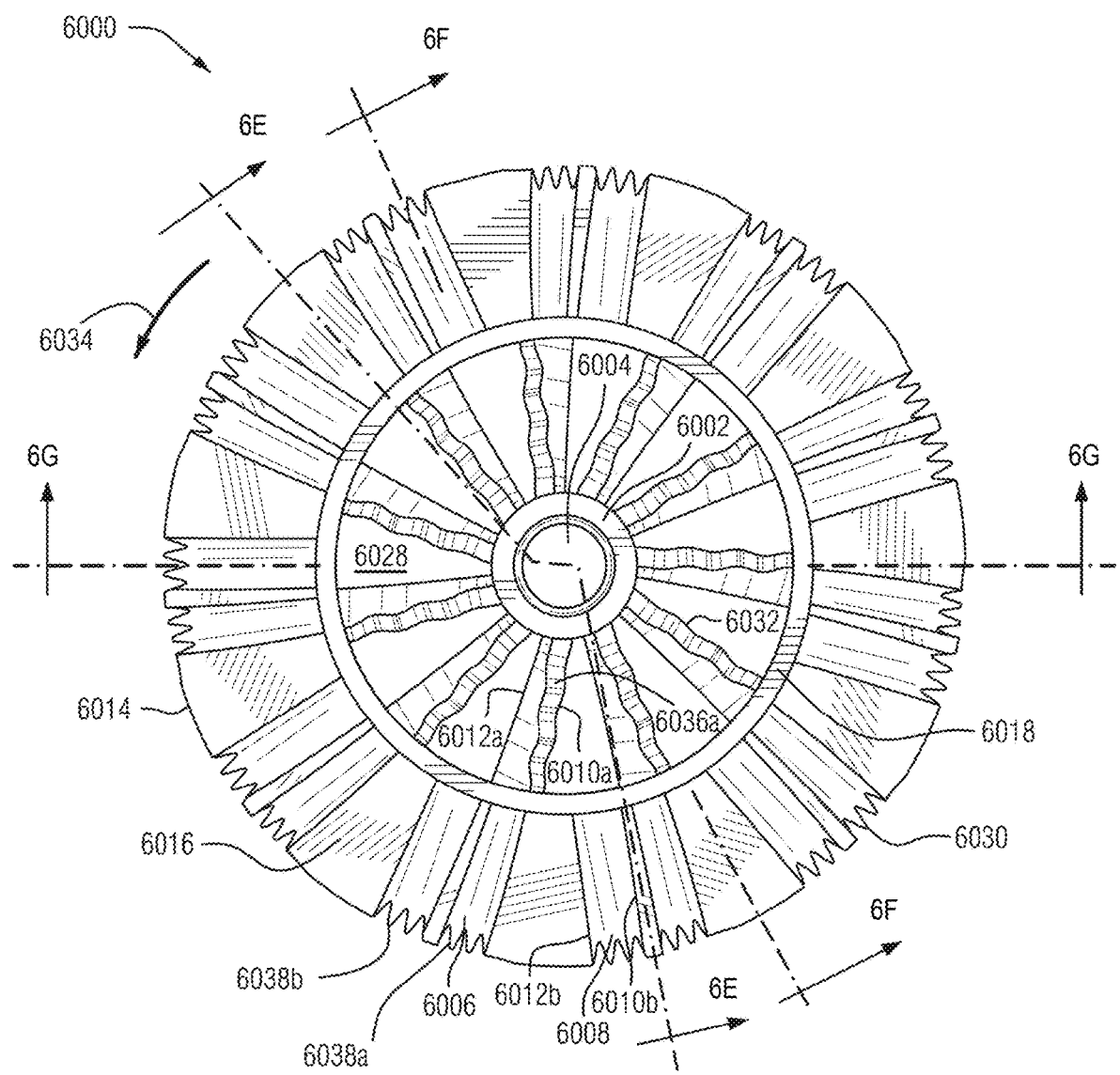

FIG. 6C shows a top view of the impeller.

Figure 6D:
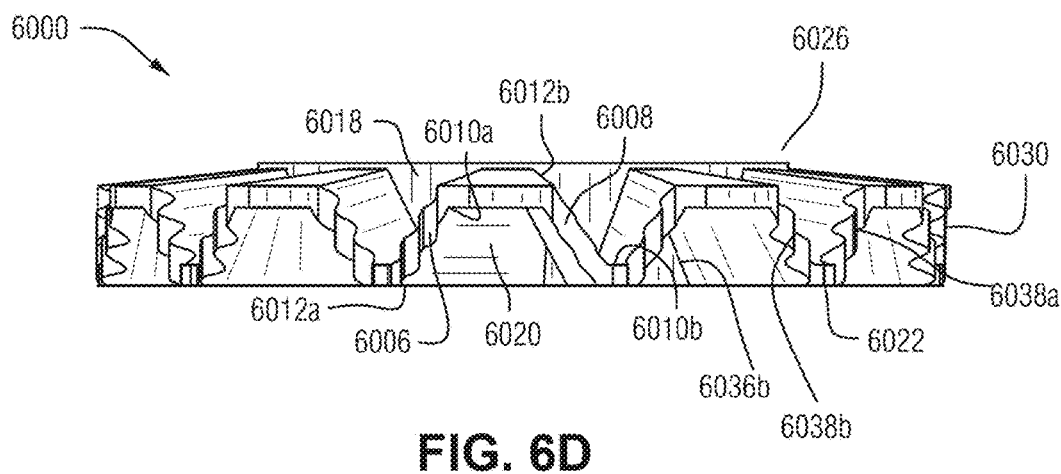

FIG. 6D shows a side view of the impeller.

Figure 6E:
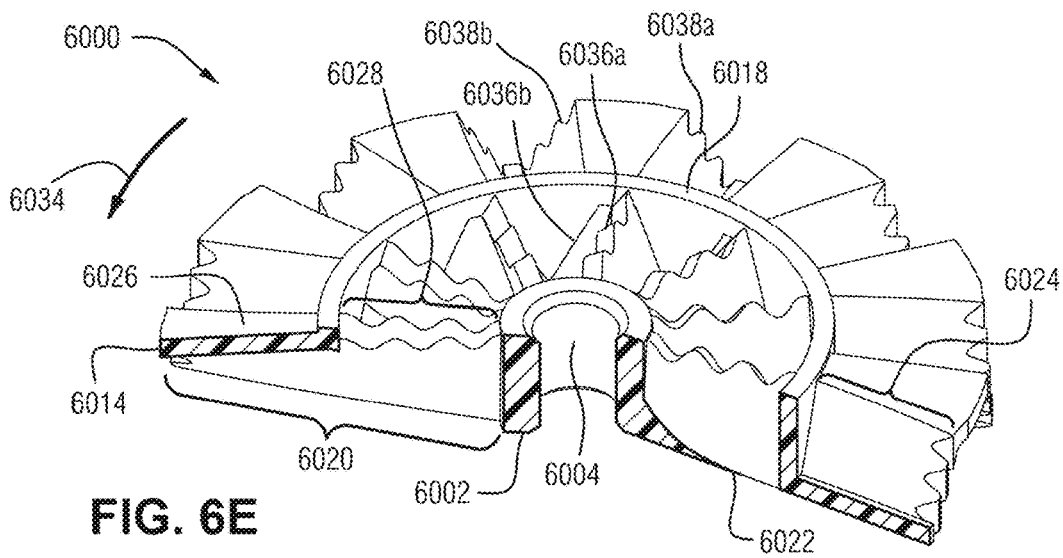

FIG. 6E shows a sectional view taken along line 6E-6E of FIG. 6C.

Figure 6F:
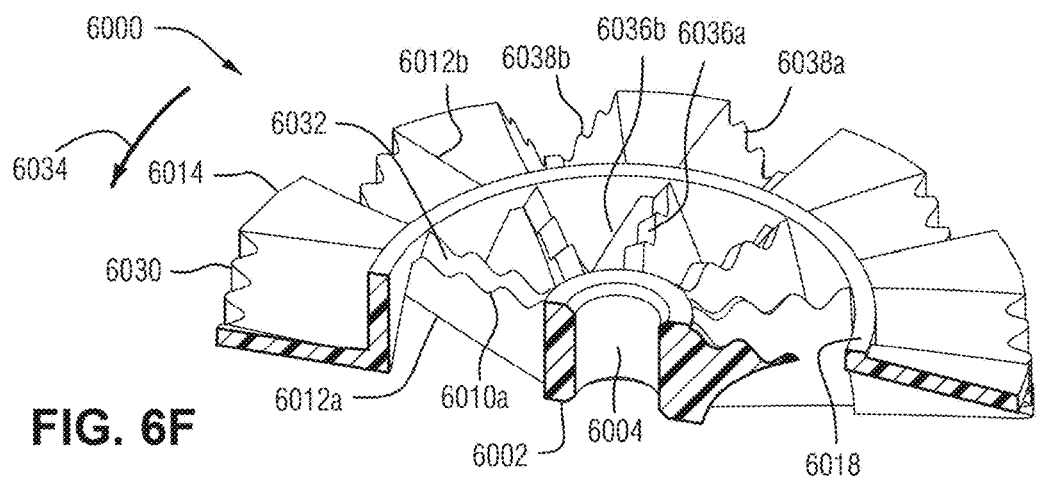

FIG. 6F shows a sectional view taken along line 6F-6F of FIG. 6C.

Figure 6G:
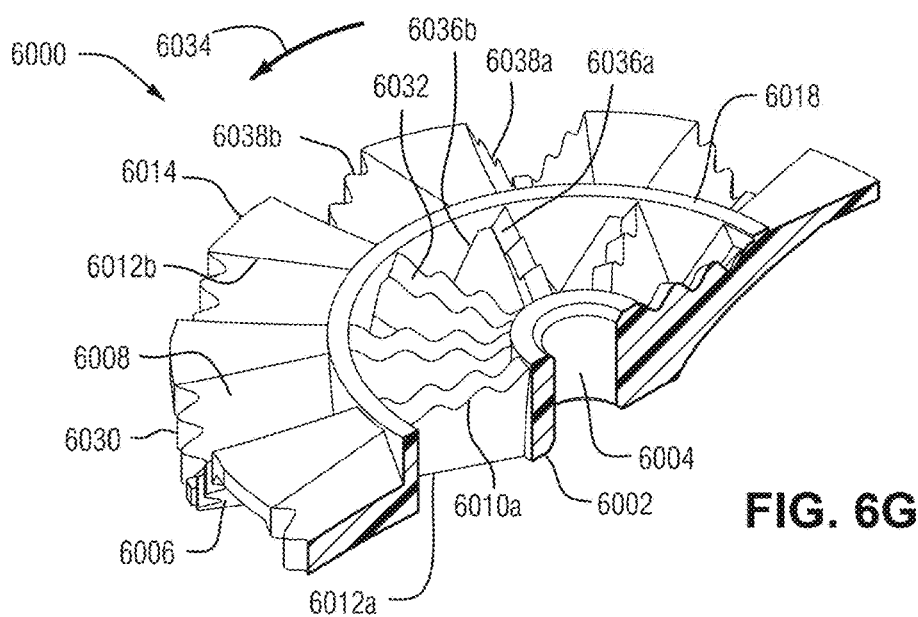

FIG. 6G shows a sectional view taken along line 6G-6G of FIG. 6C.

Figure 6H:
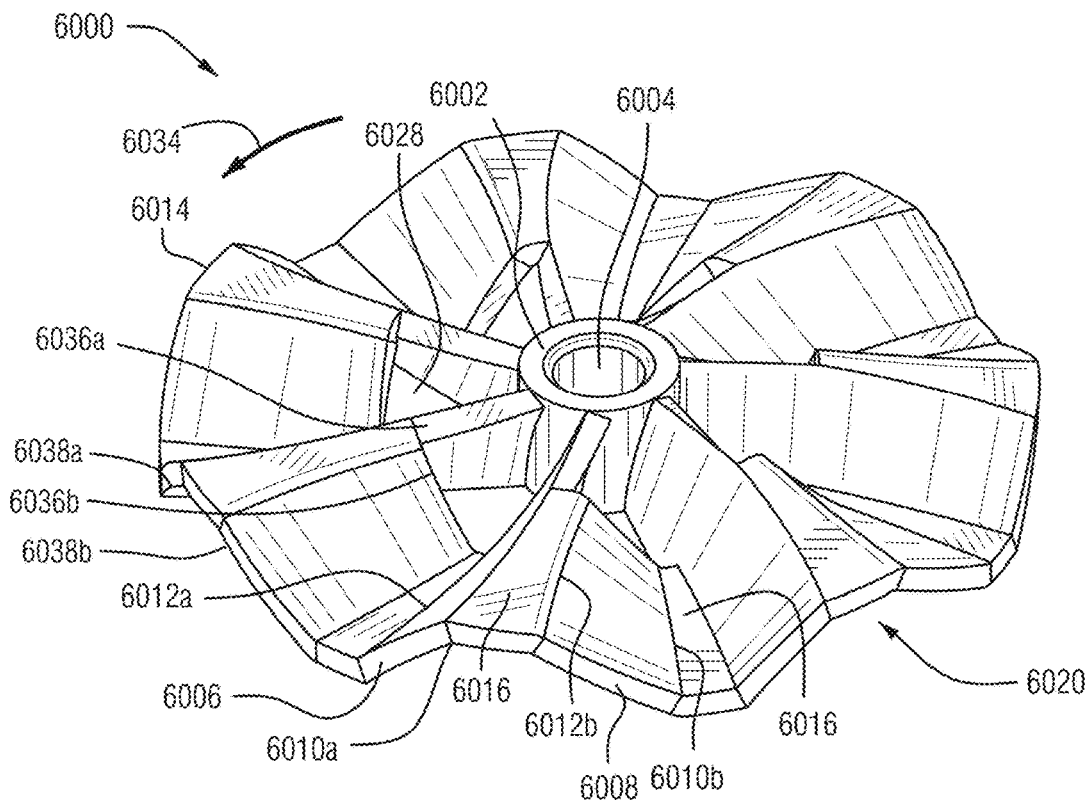

FIG. 6H shows a perspective view of an impeller suitable for use with a blower in an RPT device.

Figure 6I:
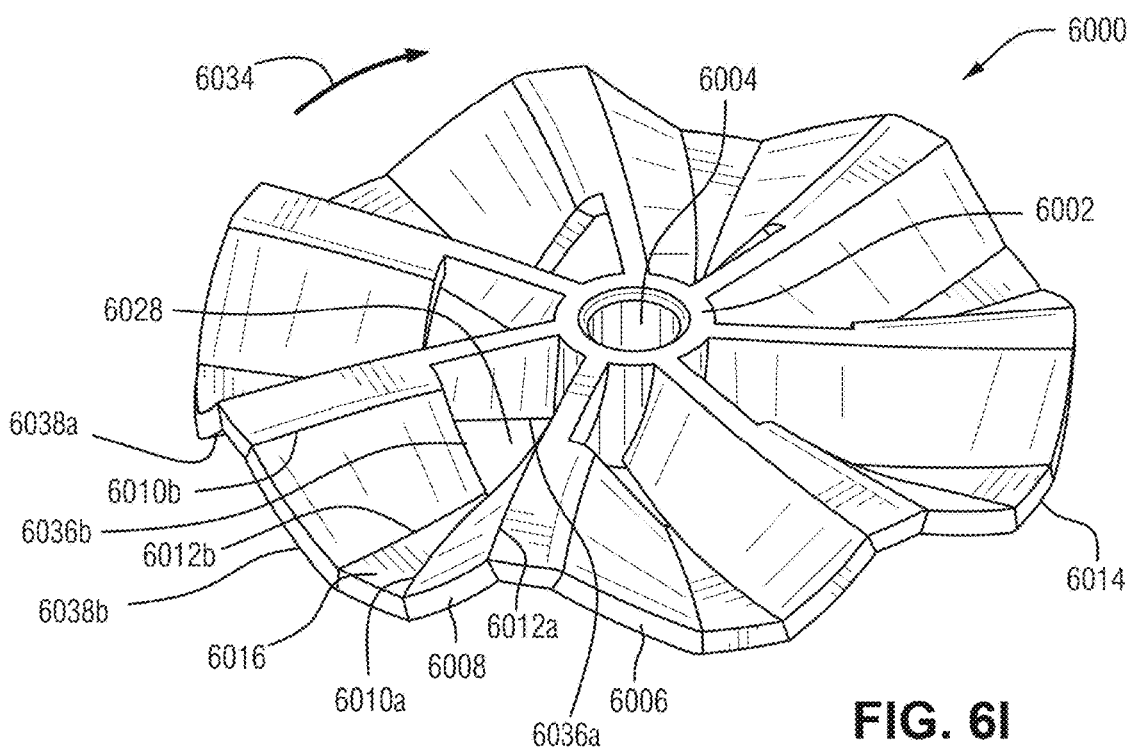

FIG. 6I shows another perspective view of the impeller viewed from an opposite side from that illustrated in FIG. 6H.

Figure 6J:
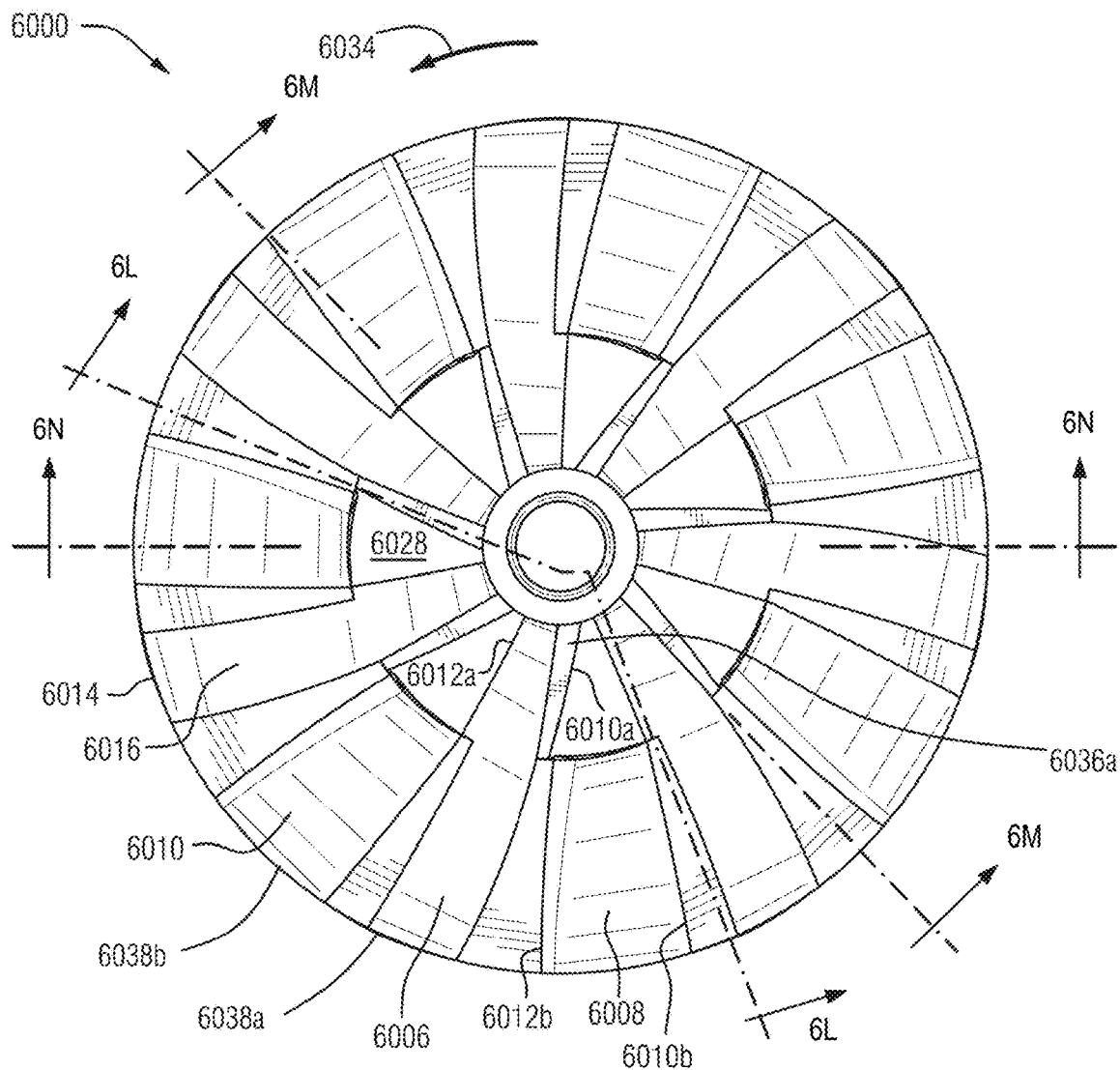

FIG. 6J shows a top view of the impeller.

Figure 6K:
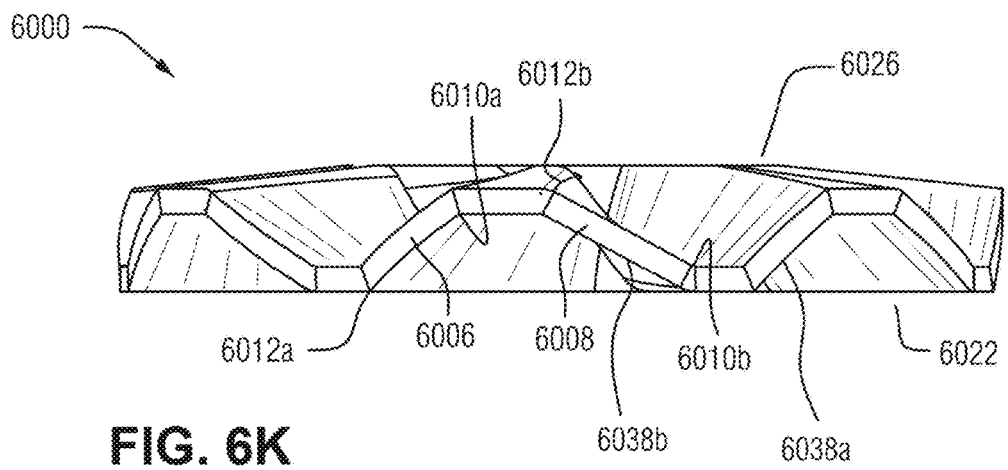

FIG. 6K shows a side view of the impeller.

Figure 6L:
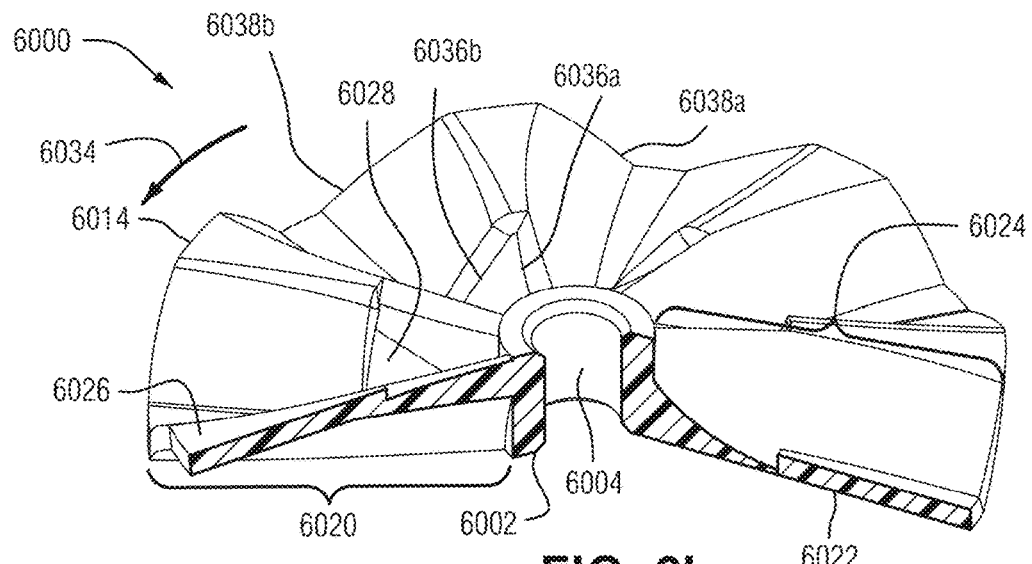

FIG. 6L shows a sectional view taken along line 6L-6L of FIG. 6J.

Figure 6M:
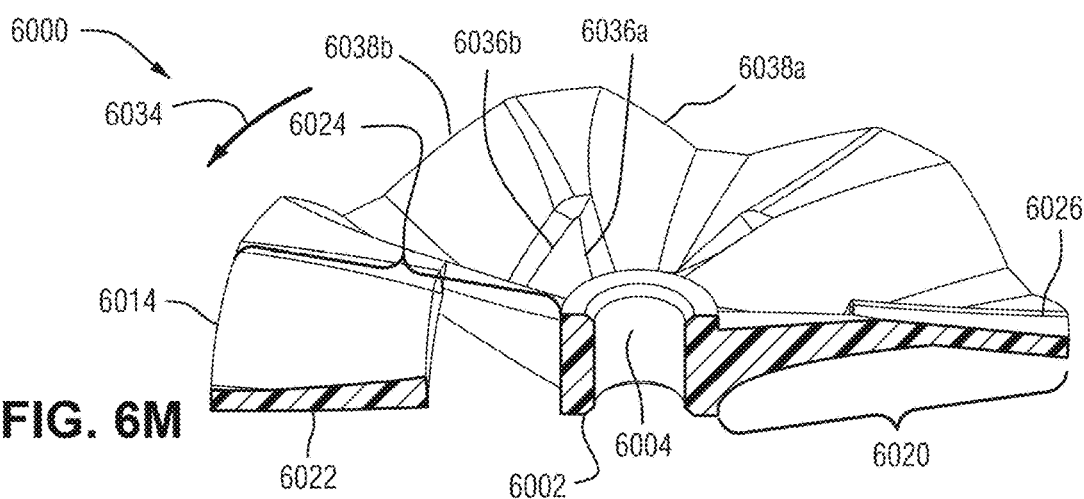

FIG. 6M shows a sectional view taken along line 6M-6M of FIG. 6J.

Figure 6N:
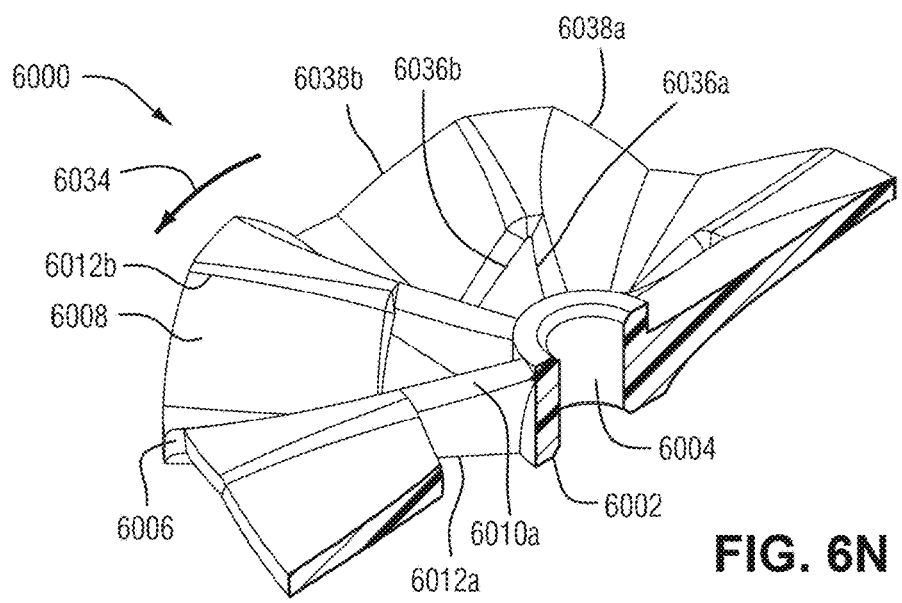

FIG. 6N shows a sectional view taken along line 6N-6N of FIG. 6J.

Figure 7A:
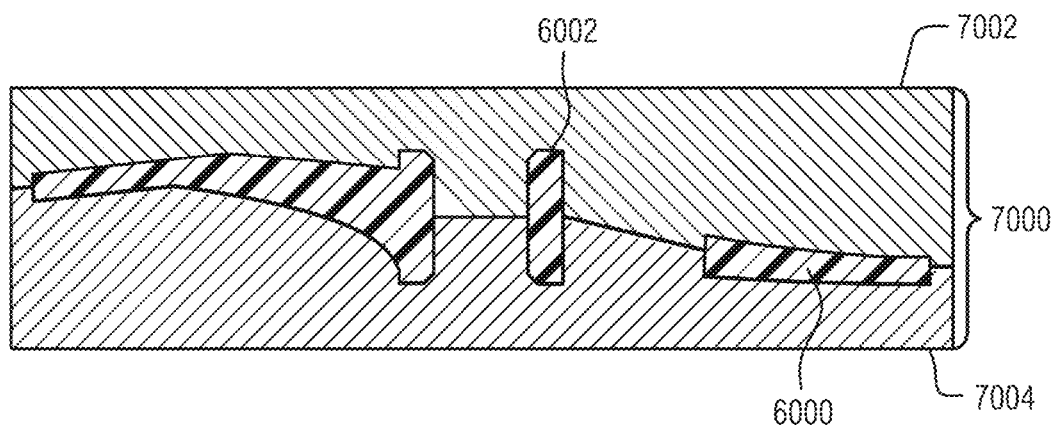

FIG. 7A shows a sectional view of a mould with an impeller in the mould.

Figure 7B:
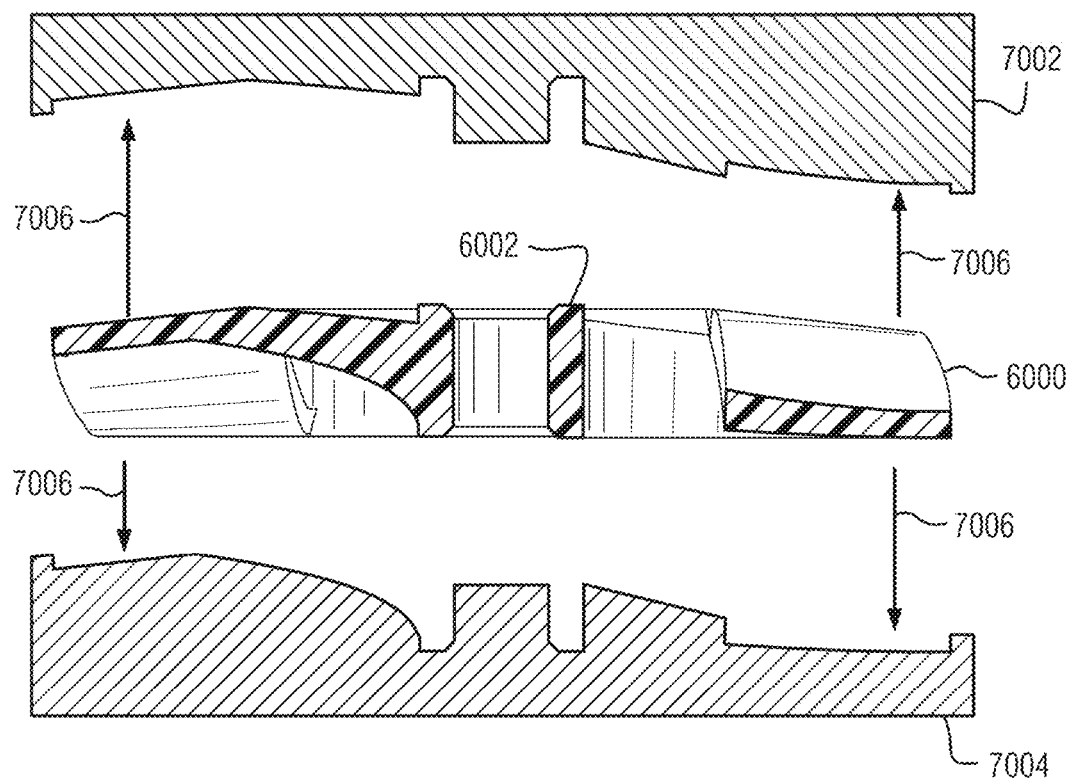

FIG. 7B shows the mould and impeller of FIG. 7A with the mould opened.

Figure 8A:
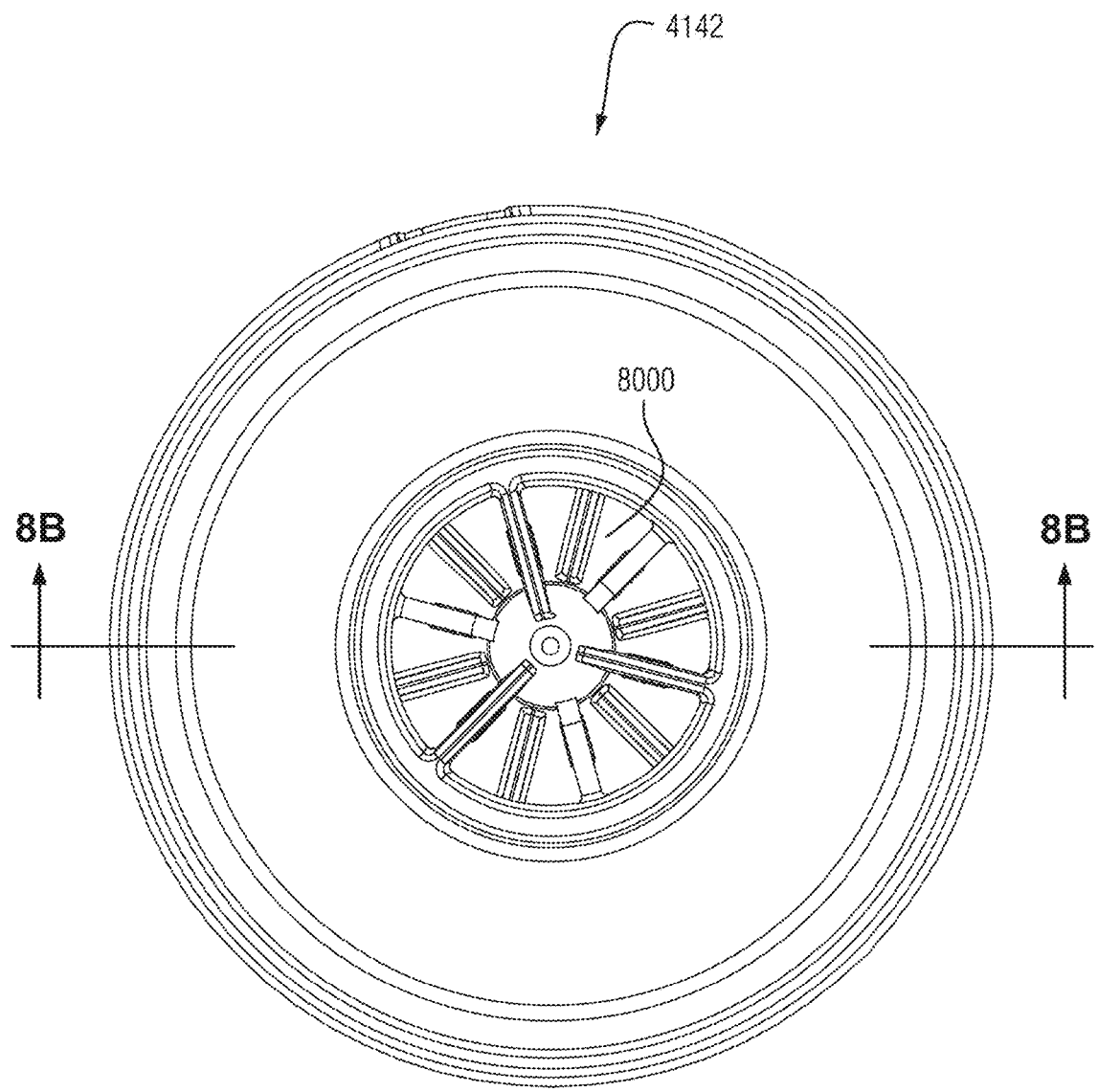

FIG. 8A shows an end view of a blower.

Figure 8B:
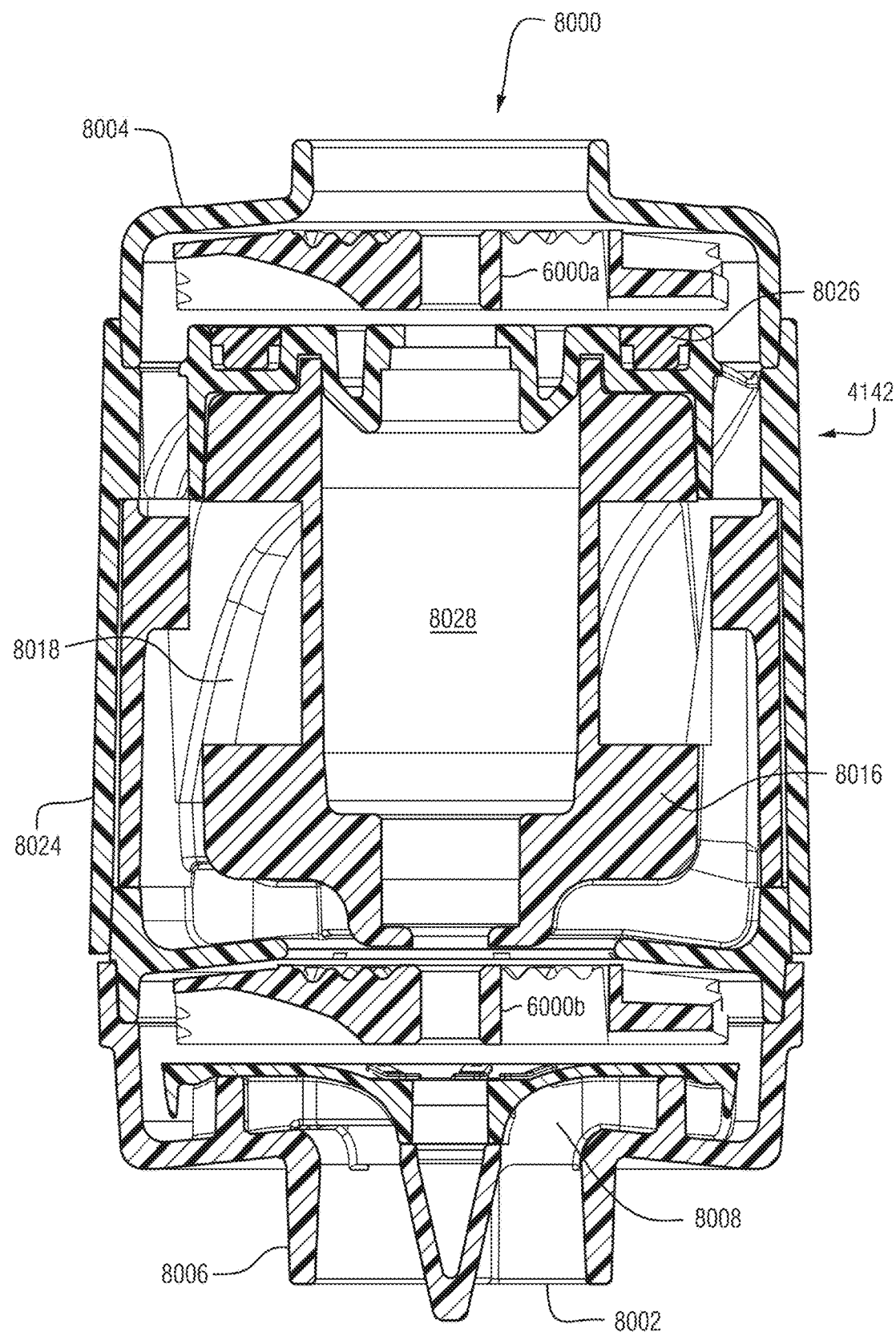

FIG. 8B shows a section of a blower taken along line 8B-8B of FIG. 8A.

Figure 8C:
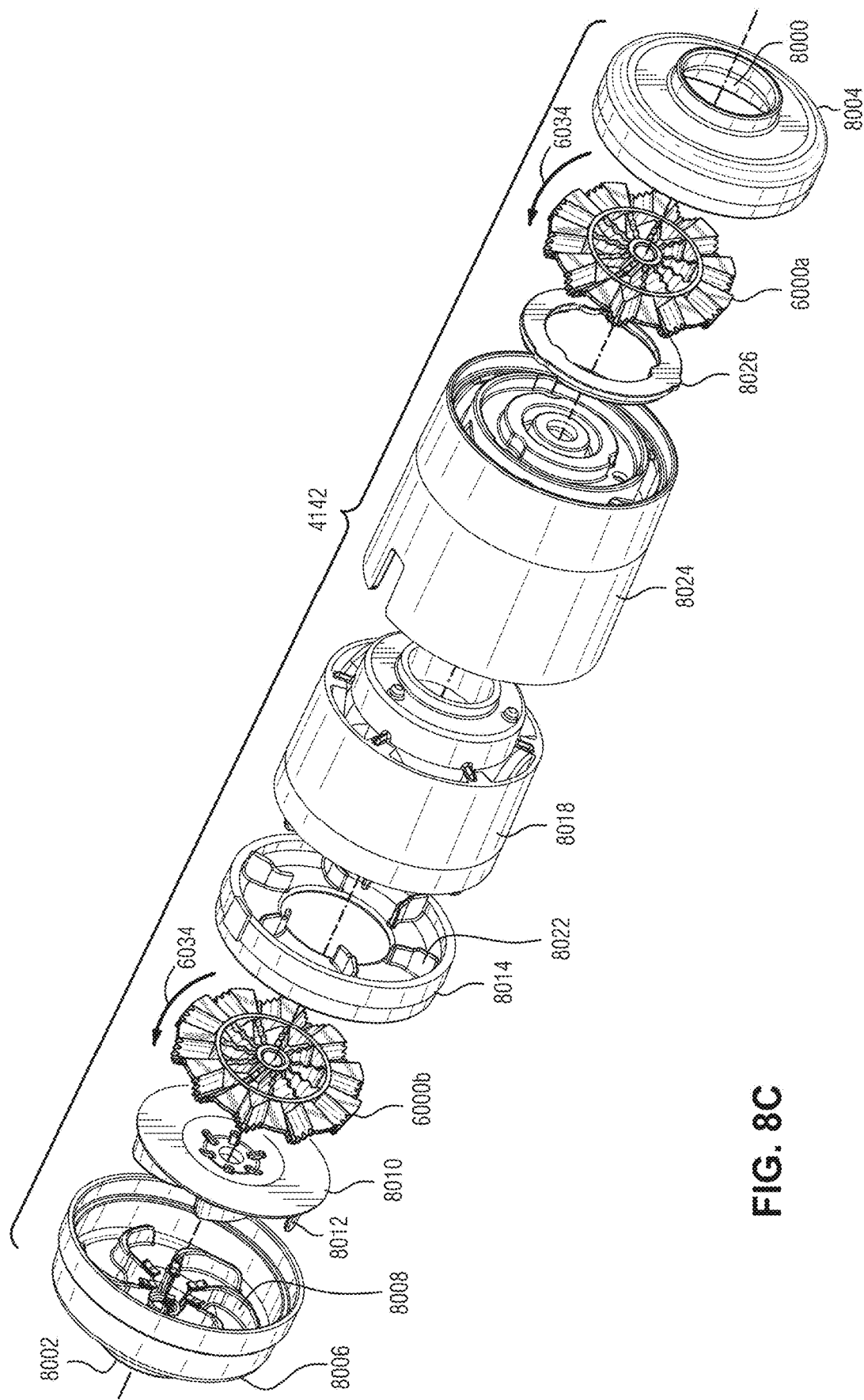
Figure 8D:
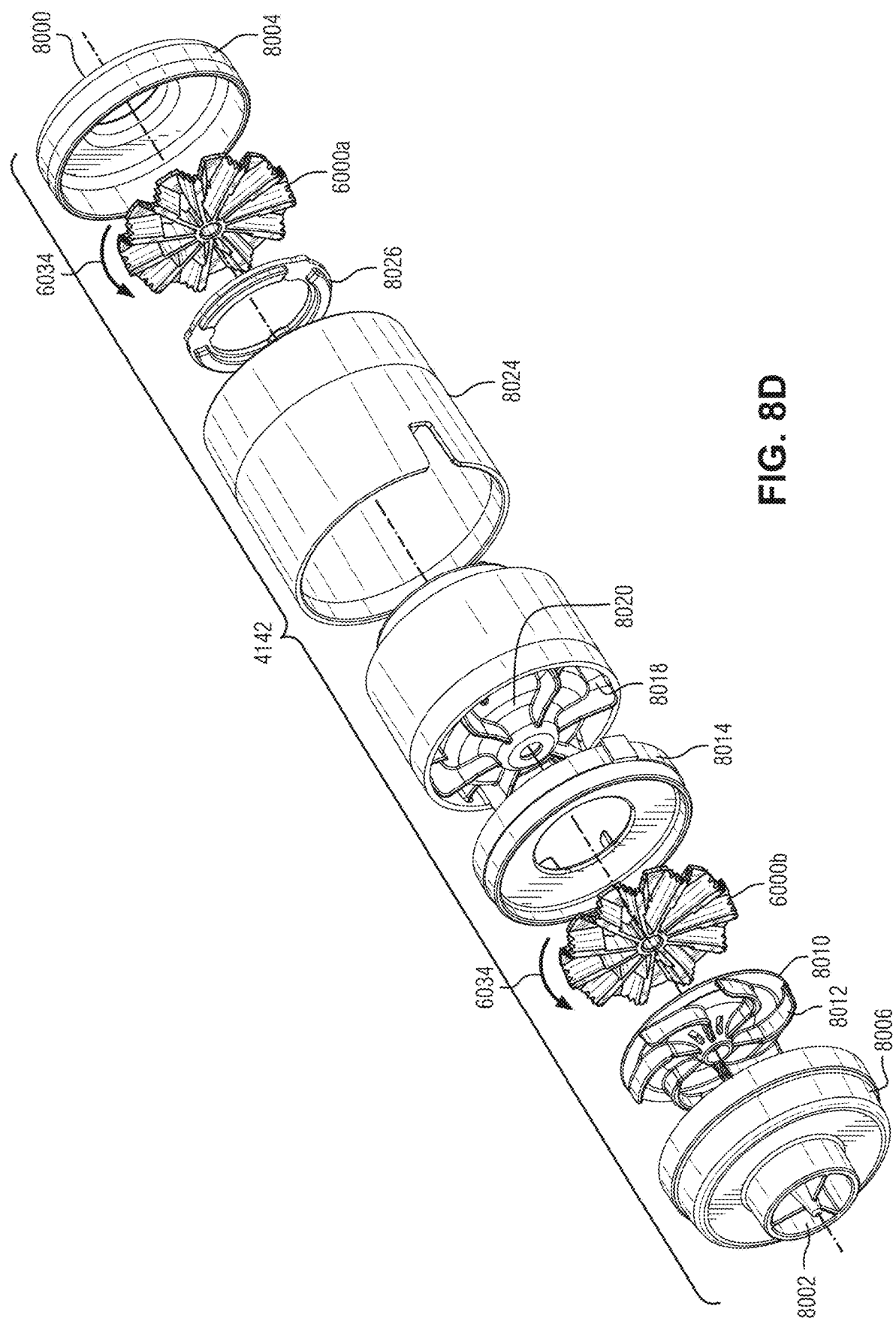

FIGS. 8C and 8D show exploded views of the blower of FIGS. 8A and 8B.

Figure 9A:
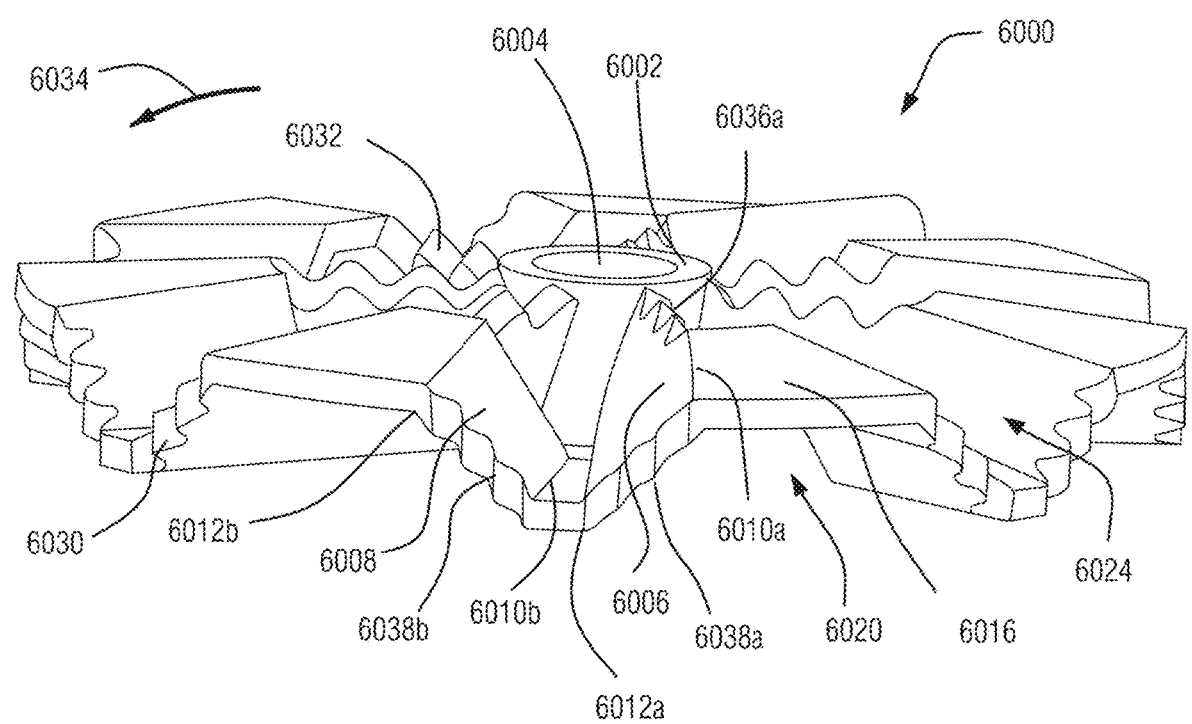

FIG. 9A shows a perspective view of a computational fluid dynamics (CFD) model of an impeller suitable for use with a blower in an RPT device.

Figure 9B:
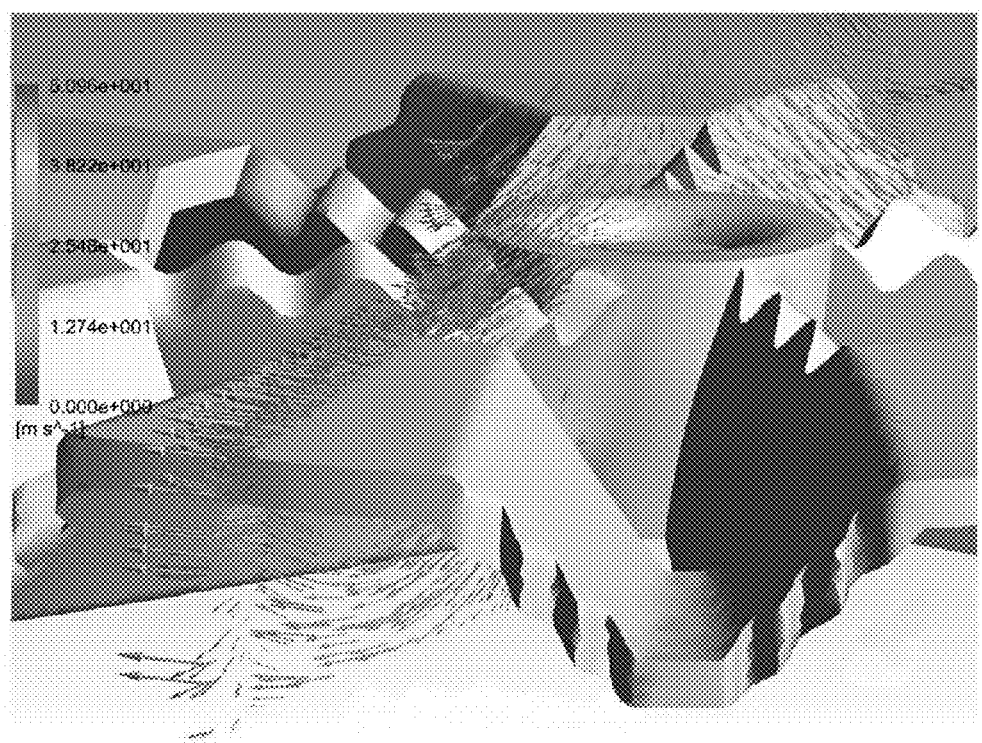

FIG. 9B shows a perspective view of a CFD model of an impeller suitable for use with a blower in an RPT device, showing relative velocity vectors in a plane.

Figure 9C:
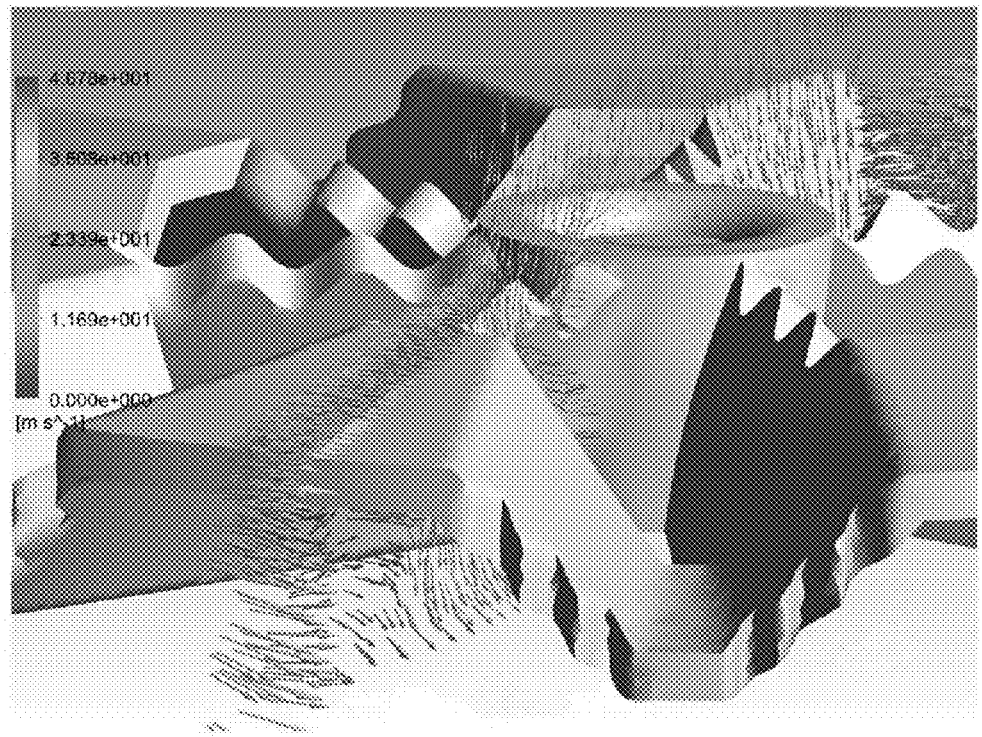

FIG. 9C shows a perspective view of a CFD model of an impeller suitable for use with a blower in an RPT device, showing absolute velocity vectors in a plane.

Figure 9D:
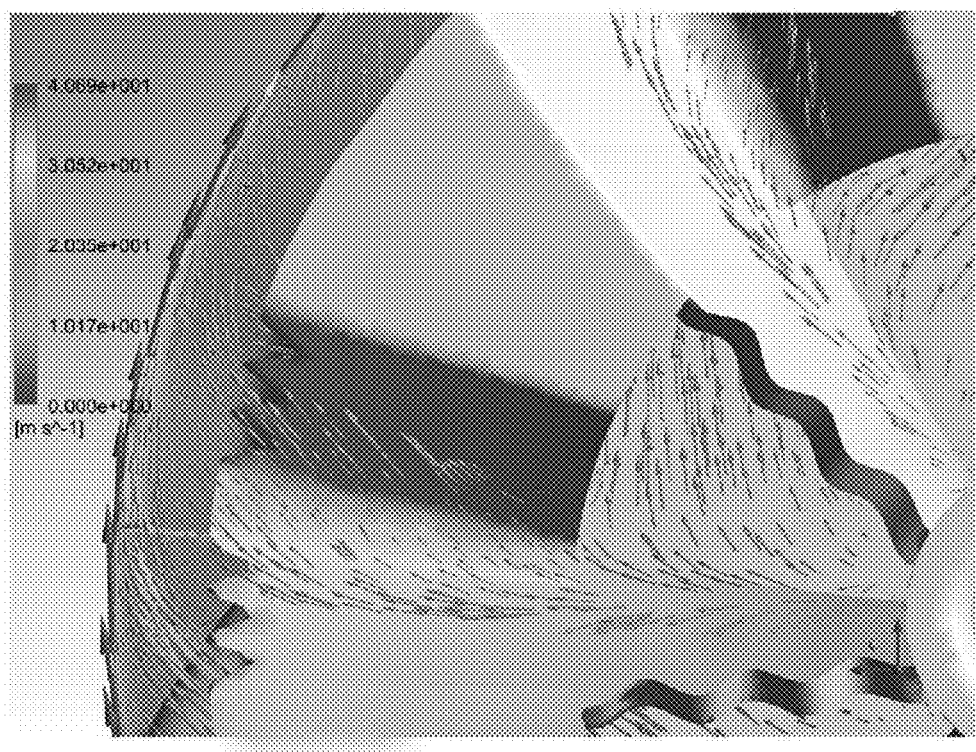

FIG. 9D shows a close-up top view of a CFD model of an impeller suitable for use with a blower in an RPT device, showing relative velocity vectors in a plane.

Figure 9E:
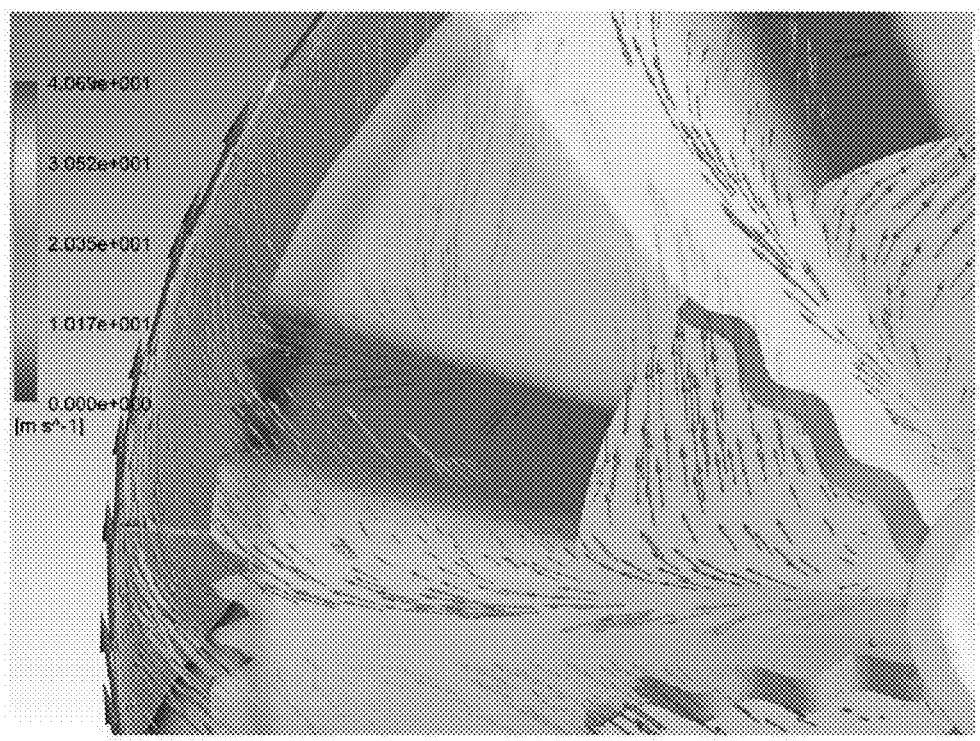

FIG. 9E shows a close-up top view of a CFD model of an impeller suitable for use with a blower in an RPT device, showing relative velocity vectors in a plane, and showing the impeller with partial transparency.

Figure 9F:
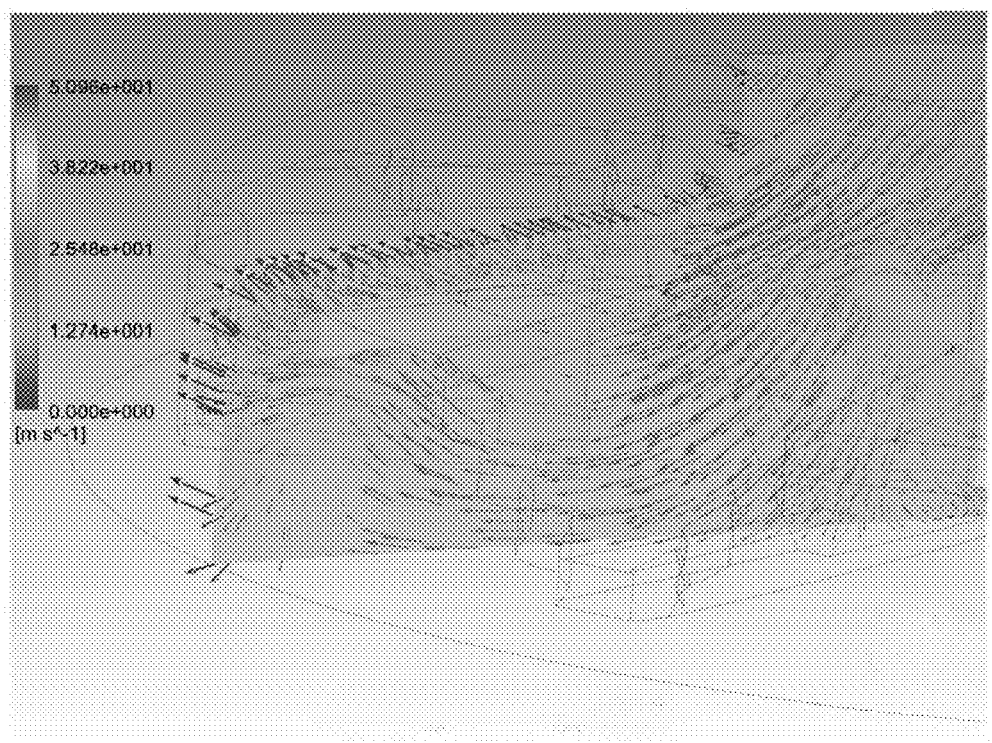

FIG. 9F shows a perspective view of a CFD model of an impeller suitable for use with a blower in an RPT device, showing the impeller in wireframe and relative velocity vectors in a plane including the primary air passage.

Figure 9G:
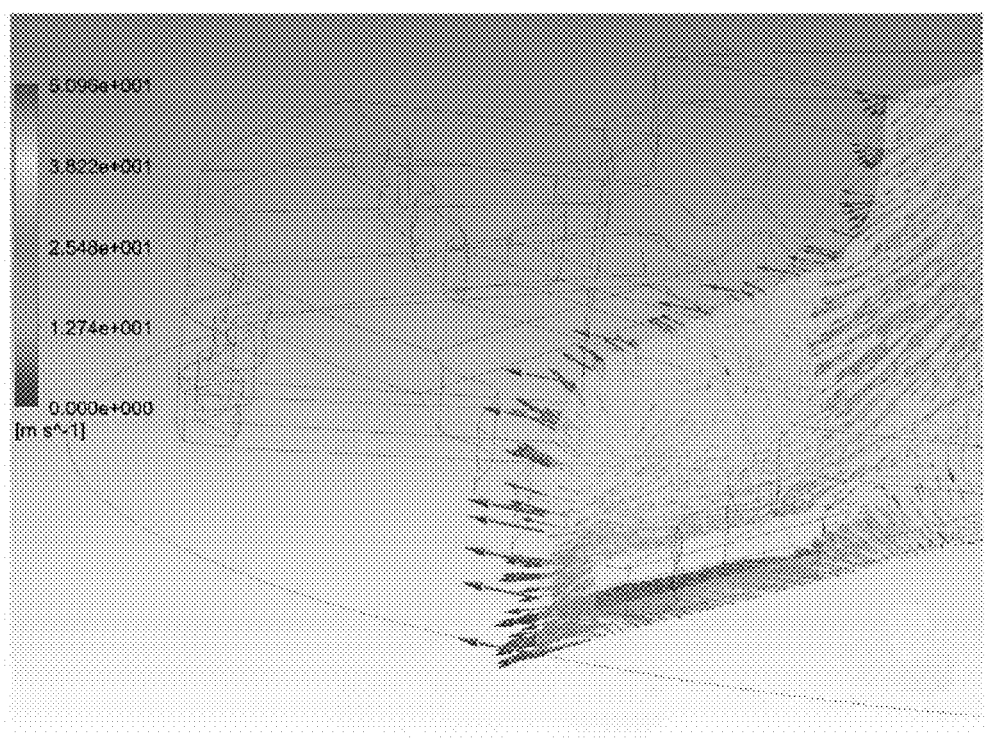

FIG. 9G shows a perspective view of a CFD model of an impeller suitable for use with a blower in an RPT device, showing the impeller in wireframe and relative velocity vectors in a plane including the secondary air passage.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.4 RPT Device

An RPT device 4000 in accordance with one aspect of the present technology comprises mechanical and pneumatic components 4100, electrical components 4200 and is configured to execute one or more algorithms. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Components

An RPT device may comprise one or more of the following components in an integral unit. In an alternative form, one or more of the following components may be located as respective separate units.

4.4.1.1 Pressure Generator

In one form of the present technology, a pressure generator 4140 for producing a flow, or a supply, of air at positive pressure is a controllable blower 4142. For example the blower 4142 may include a brushless DC motor 4144 with one or more impellers, for example housed in a casing. The casing may comprise an air inlet and an air outlet. One example of such a casing may be a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. Examples of suitable blowers may include those described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

Examples of the impeller 6000 are illustrated in FIGS. 6A-6N. The impeller 6000 may be configured for use in a centrifugal blower. As a convention herein, a 'top' side of an impeller may be defined as the side of the impeller comprising an air inlet (i.e. upstream side), and correspondingly the 'bottom' side would be the opposing side.

The impeller 6000 includes a hub 6002 with a hole 6004 that defines an axis of rotation for the impeller 6000. The hole 6004 may accept a shaft that rotatably supports the impeller 6000 although the impeller 6000 could be supported by any means that allows rotation.

The impeller 6000 includes a plurality of inclined blades 6006 and a plurality of reverse inclined blades 6008 extending in a direction radially outward from the hub 6002. As used herewithin, 'inclined blades' will be used to describe impeller blades with a bottom edge that is orientated further backward (e.g., rotationally rearward) in the preferred direction of rotation 6034 in comparison to the top edge (e.g., rotationally forward). Conversely, impeller blades with a bottom edge that is oriented further forward (e.g., rotationally forward) in the preferred direction of rotation 6034 in comparison to the top edge (e.g., rotationally rearward) will be described as 'reverse inclined blades'. Only one feature common to all of the inclined blades 6006 and reverse inclined blades 6008 is labelled per figure to improve the clarity of the figures.

A blade may comprise one continuous surface or a portion, such as shown in FIG. 6A. It is noted, however, that in some arrangements of the present technology, a blade may comprise a plurality of discontinuous surfaces or portions, such as two inclined portions, both of which may comprise a bottom edge that is oriented further backward in the intended direction of rotation in comparison to the top edge, such as a first portion inclined at 40 degrees and a second portion inclined at 60 degrees. Thus at least a portion of an aerodynamic surface of an inclined blade 6006 or a reverse inclined blade 6008 is neither parallel nor perpendicular to an axis of rotation of the impeller.

As shown in examples of the present technology (e.g. see FIGS. 6D and 6K), a blade may comprise a curved surface, or a flat surface on the topmost side of the blade. For example, a curved surface may comprise a curvature, or twist, about an axis oriented substantially in a radial direction of the impeller. In another example, a flat surface may assume a shape of a flat plane.

One aspect of the present technology relates to an impeller 6000 comprising a plurality of inclined blades 6006 extending outward from the hub 6002. Each of the plurality of inclined blades 6006 may be joined to an adjacent inclined blade 6006 at least in part by a reverse inclined blade 6008. For example, an inclined blade 6006 may be joined to an adjacent inclined blade 6006 by a reverse inclined blade 6008 and by a sector 6016. In another example, an inclined blade 6006 may be joined to an adjacent inclined blade 6006 by a reverse inclined blade 6008.

Accordingly, an impeller 6000 according one aspect of the present technology may comprise a plurality of inclined blades 6006 while the impeller 6000 remains in a line of draw. Thus, advantageously, an impeller 6000 according to the present technology may be produced by injection moulding thereby lowering a cost of manufacture.

Inclined blades 6006 and reverse inclined blades 6008 are indicated in FIGS. 6A, 6C, 6H and 6J, wherein a preferred direction of rotation 6034 of the impellers is an anti-clockwise direction as shown in the aforementioned figures. Unless stated otherwise, a 'pair' of blades herewithin will be understood to comprise an inclined blade 6006 and a complementary, adjacent, reverse inclined blade 6008.

Although eleven of the inclined blades 6006 and eleven of the reverse inclined blades 6008 (e.g., eleven pairs of blades) are illustrated in FIGS. 6A-6G, one of ordinary skill would appreciate that the number may be varied based upon design factors such as size, operating speeds of the impeller, air velocities and flow rates through the impeller 6000 and pressures generated by the impeller 6000. For example, FIGS. 6H-6N illustrate a configuration with seven inclined blades 6006 and seven reverse inclined blades 6008 (e.g. seven pairs of blades).

In some forms, the impeller 6000 may comprise an odd number of pairs of blades. In some forms, the impeller may comprise a prime number of pairs of blades. The choice of an odd (or a prime) number of pairs of blades may advantageously discourage interaction between periodic vibrations (e.g. noise and/or mechanical vibrations) related to blades and periodic vibrations of other blower/motor components.

In an example, the blower may be structured to provide pressurized air up to 45-50 cmH$_2$O, e.g., in the range of 2-50 cmH$_2$O, e.g., 3-45 cmH$_2$O, 3-30 cmH$_2$O, 3-20 cmH$_2$O. The impeller may for example spin at up to 60,000 rpm, such as at up to 50,000 rpm, or 40,000 rpm. In some example, the impeller may comprise a diameter of approximately 20 to 50 mm, such as 20 mm, 25 mm, 30 mm, 40 mm or 50 mm or any value in between. It will of course be understood that size and speed of an impeller may be varied. For example, an impeller spinning at 40,000 rpm with a diameter of 30 mm may produce a pressure output comparable to an impeller spinning at 30,000 rpm with a diameter of 40 mm.

The inclined blades 6006 are illustrated as directly connected to the hub 6002 (i.e. to extend from the hub 6002) whereas the reverse inclined blades 6008 are illustrated as connected to the hub by way of the inclined blades 6006. However, this configuration could be reversed such that the reverse inclined blades 6008 are directly connected to the hub 6002 with the inclined blades 6006 being connected to the hub 6002 by way of the reverse inclined blades 6008. Alternatively, both the inclined blades 6006 and the reverse inclined blades 6008 may be directly connected to the hub 6002. In another alternative, an intervening structure (not illustrated) may connect one or both of the inclined blades 6006 and the reverse inclined blades 6008 to the hub 6002. For example, an impeller may comprise a shroud that extends radially from the hub, and inclined blades and/or reverse inclined blades that are connected to the shroud.

Each blade includes a leading edge and a trailing edge. Typically, the term 'leading edge' is used to describe the most upstream edge of an aerofoil for the air flow. Conversely, 'trailing edge' is used to describe the most downstream edge of an aerofoil for the air flow.

In one example of the present technology, the impeller 6000 is used as a centrifugal blower 4142 as shown in FIG. 8A-8D, comprising an inlet 8000 located towards a centre of the impeller.

FIGS. 9A-9G show images from computational fluid dynamics (CFD) modelling/simulations of an exemplary blower comprising two impellers. In the model shown, the blower is modelled comprising two impellers each rotating at 25,000 rpm. It will be of course understood that the CFD model is illustrated to indicate the air flow behaviour generally for blowers according to the present technology. It will also be understood that the particular flow characteristics may vary, for example according to geometry or boundary conditions applied.

FIG. 9A shows an impeller 6000 from the CFD model from which cross sections were taken at which velocity vector profiles were generated in subsequent figures.

The arrows shown in FIGS. 9B-9I indicate a direction of the airflow at the origin of the arrow, as well as a magnitude of the air velocity. Reference numbers are omitted from these figures for clarity.

FIG. 9B shows a plot of air velocity vectors in a rotating reference frame, wherein the reference frame is rotating with the impeller (which is rotating). That is, the air velocity vectors indicated show air velocity relative to the impeller. Air velocity vectors plotted in this manner (in a rotating reference frame) will be referred to as relative vectors.

In comparison, FIG. 9C shows a plot of air velocity vectors in a stationary reference frame. That is, the air velocity vectors indicated show air velocity relative to a stationary reference. Air velocity vectors plotted in this manner (in a stationary reference frame) will be referred to as absolute vectors. Thus, the impeller shown in FIGS. 9B and 9C are rotating in an anti-clockwise direction. The velocity vectors in FIGS. 9B and 9C show the air flow to travel from the inlet 8000 primarily in an axial direction prior to entering the impeller 6000.

FIGS. 9D and 9E plot relative velocity vectors on a radially extending cross-sectional plane, which show that the air flow travels on either side of each blade. The impeller in FIGS. 9D and 9E is rotating in an anti-clockwise direction. FIG. 9D illustrates the impeller in opaque, and FIG. 9E illustrates the impeller to be semi-transparent, such that FIG. 9E shows the air flow in the primary air passage (described in further detail below).

Thus, each inclined blade 6006 comprises a leading edge 6036a and a trailing edge 6038a, and each reverse inclined blade 6008 comprises a leading edge 6036b and a trailing edge 6038b. Each inclined blade 6006 comprises a rotationally forward edge 6010a and a rotationally rearward edge 6012a. Each reverse inclined blade 6008 includes a rotationally forward edge 6010b and a rotationally rearward edge 6012b. In the illustrated configurations, a portion of the rotationally forward edge 6010a is coincident with the leading edge 6036a.

The term "edge" as used in this manner refers to a functional boundary, which may or may not also form a physical boundary. As can be seen, for example, in FIGS. 6A and 6B, the rotationally forward edge 6010a forms a physical boundary near the hub 6002 because the rotationally forward edge 6010a is not continuously connected to another structure in a circumferential direction. Conversely, the rotationally forward edge 6010a is continuously connected to another structure in a circumferential direction near the outer perimeter 6014 (or periphery) of the impeller 6000. Due at least in part to an arrangement of the inlet 8000 wherein its radius is smaller than that of an inclined blade 6006, only a portion of the inclined blade 6006 is incident with the air flow as it enters the impeller, thereby functionally acting as a leading edge 6010a as shown.

Thus at least near the perimeter 6014, the plurality of inclined blades 6006 and the plurality of reverse inclined blades 6008 form a plurality of pairs of blades. Each of the top and bottom of each inclined blade 6006 and reverse inclined blade 6008 may converge towards an adjacent edge of an adjacent blade. Each pair of inclined blade 6006 and reverse inclined blade 6008 thus forms a structure that is substantially V-shaped when viewed from a radially outward end of the pair. At or near a leading edge 6036a of an inclined blade, the inclined blade may not be connected to a corresponding reverse inclined blade, forming an opening 6028 as further described elsewhere in the present document.

The inclined blades 6006 form a negative angle with respect to the axis of rotation and the reverse inclined blades 6008 form a positive angle with respect to the axis of rotation; however, this should not be considered limiting and instead should be understood to only describe the relative relationships of the inclined blades 6006 and reverse inclined blades 6008. In an example of the present technology, the positive angle and the negative angle may have the same absolute value. Alternatively, the absolute value of the angles may be different. The impeller illustrated in the present figures is intended to rotate in a first direction but it will be appreciated that an impeller can be designed to rotate in the opposite direction and to do so the angles of the inclined blades 6006 and reverse inclined blades 6008 may be reversed.

The angle formed by the inclined blades 6006 with respect to the axis of rotation may be constant along the entire radial length of the plurality of inclined blades 6006. The angle formed by the reverse inclined blades 6008 with respect to the axis of rotation may be constant along the entire radial length of the plurality of reverse inclined blades 6008. Alternatively, one or both angles can vary along the lengths of the inclined blades 6006 and reverse inclined blades 6008. For example, one or more of the angle of the inclined blades 6006 and the angle of the reverse inclined blades 6008 (with respect to the axis of rotation) may be configured to increase as the radius increases. The inclined blades may be angled with respect to the axis of rotation between 10 and 80 degrees. For example, 20 to 70 degrees, 30 to 60 degrees, 40 to 50 degrees or any constant or varied angle in between. The reverse inclined blades may be angled with respect to the axis of rotation between −10 and −80 degrees. For example, −20 to −70 degrees, −30 to −60 degrees, −40 to −50 degrees or any constant or varied angle in between.

Each pair of inclined blade 6006 and reverse inclined blade 6008 may be connected to the two adjacent pairs of inclined blade 6006 and reverse inclined blade 6008 by a sector 6016 that is substantially perpendicular to the axis of rotation. As illustrated, the sector 6016 extends from at or near the outer perimeter 6014 towards the axis of rotation and terminates at an intermediate circumferential portion 6018. Although the sectors 6016 are illustrated as substantially perpendicular to the axis of rotation, other orientations may be utilized as well as may be dictated by the aerodynamic performance requirements of the impeller 6000. For example, the sectors 6016 could be inclined in a manner such that the sectors 6016 together form a conical shape (e.g., with the portions of the sectors 6016 at the outer perimeter 6014 being circumferentially aligned and the inner portions of the sectors 6016 at the intermediate circumferential portion 6018 being circumferentially aligned but axially offset from the outer perimeter 6014). As a second example, the sectors 6016 could be inclined or reverse inclined similar to but at a different angle from the inclined blade 6006 or reverse inclined blade 6008.

Although the sectors 6016 are illustrated between the top side of inclined blades 6006 and the top side of the adjacent reverse inclined blades 6008 in FIGS. 6A-6G, the sectors 6016 may also be provided between the bottom side of inclined blades 6006 and the top bottom of the adjacent reverse inclined blades 6008 as illustrated in FIGS. 6H-6N. The sectors 6016 may be included or omitted if the aerodynamic performance of the impeller 6000 in a given application so dictates. For example, the sectors 6016 illustrated in FIGS. 6H-6N may be reduced in size and/or the inclined blades 6006 and reverse inclined blades 6008 may be oriented to eliminate the sectors 6016 altogether.

In impellers, periodic pressure pulses may be generated due to a periodic passage of each blade. In prior art impellers, wherein its blades comprise trailing edges configured in parallel to its adjacent casing, passage of a blade against a portion of the casing may produce a short, discrete pressure pulse event. Particularly, when such an impeller is adopted in a respiratory pressure therapy device (e.g. a PAP device), the pressure pulse(s) may be perceived as noise, which may increase a risk of the patient not adopting the use of the device.

Advantageously, inclination of the trailing edge 6012a of the inclined blades 6006 and/or the trailing edge 6012b of the reverse inclined blades 6008 may skew pressure pulses coming off of tips of the plurality of inclined blades thereby reducing noise. The skewed pressure pulse may reduce the synchronicity of pressure fluctuations that are created by passage of each portion of the blade.

As best viewed in FIGS. 6E and 6L, the arrangement discussed above provides a first flow path 6020 (e.g., a primary air passage) on a first face 6022 of the impeller 6000 that extends in a direction from the hub 6002 to the outer perimeter 6014. The first flow path 6020 may extend from the hub 6002 to the outer perimeter 6014. FIG. 9F shows an exemplary plot of relative air velocity vectors through a cross section that includes a first flow path 6020, showing the impeller in wireframe.

A second flow path 6024 (e.g., a secondary air passage) on a second face 6026 of the impeller 6000 extends in a direction from the hub 6002 towards the outer perimeter 6014. The second flow path 6024 is illustrated as extending only from the intermediate circumferential portion 6018 to the outer perimeter 6014 (see, e.g., FIGS. 6A to 6G) but the second flow path 6024 may extend from the hub 6002 to the outer perimeter 6014 if, for example, the intermediate circumferential portion is omitted (see, e.g., FIG. 6H to 6N) or if an aperture is provided through the intermediate circumferential portion 6018. FIG. 9G shows an exemplary plot of relative air velocity vectors through a cross section that includes a second flow path 6024, showing the impeller in wireframe.

The impeller 6000 may include one or more openings 6028 that allow air to flow from the second face 6026, into the first flow path 6020 and radially outward. The openings 6028 may be provided between the inclined blades 6006 or the reverse inclined blades 6008 and the hub 6002. The figures illustrate an opening 6028 that extends between the reverse inclined blades 6008 and the hub 6002, appearing as though a portion of the reverse inclined blades 6008 have been omitted, in comparison to the reverse inclined blades 6008 extending to the hub 6002. Thus the reverse inclined blades are illustrated as not extending to the hub 6002. It will be appreciated that if a portion of the inclined blades 6006 is omitted, the inclined blades 6006 may not extend to the hub 6002. Alternatively, an aperture may be provided through one or both of the inclined blades 6006 and reverse inclined blades 6008. A radius of the opening(s) 6028 may be substantially identical to a radius of an inlet 8000 of the blower, such as located in the inlet cover. In one example, a radial length of a reverse inclined blade may be approximately 60% of that of an inclined blade, such as 50%, or 70%. However, such a value may vary according to a size of the blower and/or impeller.

The impeller 6000 may comprise one or more aerodynamic features, such as on one or more of: a surface of an impeller, a leading edge of a blade and a trailing edge of a blade. Examples of aerodynamic features include serrations to, for example, reduce a blade pass pulse or bumps to encourage flow attachment.

A difference between FIGS. 6A to 6G versus FIGS. 6H to 6N is that the first group of figures includes serrations 6030 at the trailing edges of both the inclined blades 6006 and at tips of the reverse inclined blades 6008. Serrations 6032 are also provided on the leading edge 6010a.

Although not illustrated, one or both of the serrations 6030, 6032 may be provided with the impellers 6000 illustrated in FIG. 6H to 6N. Similarly, the one or both of the serrations 6030, 6032 may be omitted from the impeller 6000 illustrated in FIGS. 6A to 6G. Similar serrations may be applied to a leading edge or a trailing edge of either of the inclined blades 6006 or reverse inclined blades 6008.

Another aspect of the arrangement discussed above is that the impeller 6000 can be formed without an undercut. FIGS. 7A and 7B illustrate a simplified cross-section of a mould 7000 to manufacture the impeller 6000 using injection moulding. As can be seen in these figures, the mould halves 7002, 7004 may form all of the features of the impeller 6000 without any insert because there is no undercut. In other words, all of the surface features of the impeller 6000 can be formed on one of the mould halves 7002, 7004. The line of draw 7006 (or direction that the mould halves 7002, 7004 engage and separate) may be substantially parallel to the axis of rotation defined by the hub 6002. This arrangement may be beneficial in that manufacturing costs can be reduced, from reduced tooling costs and/or cycle time.

Further advantageously, an inclined arrangement of blades as disclosed herein may allow aforementioned aerodynamic features to be more easily moulded in the line of draw. Thus, the impeller 6000 may for example comprise serrations in the inclined blade 6006 and/or the reverse inclined blade 6008 as well as being suitable for manufacture by injection moulding.

FIGS. 8A to 8D illustrate the impeller 6000 installed in a blower 4142. The blower illustrated in the drawings is an axially arranged blower. Another example of an axially arranged blower is shown in U.S. Pat. No. 7,866,944, which is incorporated by reference in its entirety. The impeller 6000 may also be used in other types of blowers such as scroll-type blowers with a radial volute, an example of which is shown in U.S. Pat. No. 8,393,320, which is incorporated by reference in its entirety. An impeller 6000 comprising a set of inclined blades and reverse inclined blades may also advantageously reduce noise when used in a radial volute. For example, a skewed pressure pulse produced by an inclined blade may reduce a noise produced at a tongue (or cut-off).

FIG. 8A illustrates an end view of the blower 4142 taken from an end with an inlet 8000 and serves as the basis for the cross-section of FIG. 8B. The blower 4142 includes the inlet 8000, an outlet 8002, a first impeller 6000a and a second impeller 6000b. The inlet 8000 is defined by an inlet cover 8004 covering the first impeller 6000a. The inlet cover 8004 forms a part of a cylindrical casing of the blower that defines the exterior boundary of the air path.

The outlet 8002 is formed by an outlet cover 8006, which includes stator vanes 8008 on an interior portion of the outlet cover. A shield 8010 (best viewed in FIGS. 8C and 8D) is disposed between the outlet cover 8006 and the second impeller 6000b. The shield 8010 includes another set of stator vanes 8012 that face the stator vanes 8008. These two sets of stator vanes may be nested within one another. The second impeller 6000b is disposed between the shield 8010 and a lower housing cover 8014, which includes another set of stator vanes 8022 (see FIG. 8C). The outlet cover 8006, shield 8010 and lower housing cover 8014 also partly define the air path.

The impellers 6000a, 6000b may be disposed on opposite ends of the motor 4144, which is not illustrated in FIGS. 8A to 8D for clarity. Instead, a motor cavity 8028 is illustrated in a motor housing 8016. The motor housing includes a further set of stator vanes 8018, which are disposed along an axial length of the motor housing 8016 (see FIG. 8B) and on an end face 8020 of the motor housing 8016 (see FIG. 9D). The stator vanes 8018 on the end face 8020 may be nested within the stator vanes 8022 on the lower housing cover 8014. The sets of stator vanes described above provide a flow path from the first impeller 6000a to the second impeller 6000b and through the outlet 8002.

In some forms, a blower 4142 may comprise a different number and/or configuration of impellers than those shown herewithin. For example, a blower 4142 may comprise one, two, three, four or more impellers. The impellers in the blower may be disposed on a first side or the second side of the motor 4144. None, some or all of impellers may be disposed on a first side of the motor 4144, with the rest being disposed on a second side of the motor 4144.

The blower 4142 also includes an end bell 8024 around the motor housing 8016 and connected to the lower housing cover 8014 and the inlet cover 8004. The end bell 8024 may support a top bearing (not illustrated) near the first impeller 6000a.

An acoustic cover 8026, which may be omitted, is disposed between the end bell 8024 and the first impeller 6000a. The acoustic cover 8026 may cover any surface imperfections (e.g. from heat staking) that may cause noise.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.4.1.2 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in United States Patent Application No. US/2011/0023874, which is incorporated herewithin in its entirety by reference.

4.5 Humidifier 4.5.1 Humidifier Overview

In one form of the present technology there is provided a humidifier 5000 (e.g. as shown in FIG. 4A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 4A and FIG. 4B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.6 Breathing Waveforms

FIG. 5 shows a breath waveform as discussed in detail below. This waveform may provide exemplary flow characteristics for determining design parameters for the present technology. For example, an impeller 6000 may be designed to respond to aspects of this waveform, which in turn may provide performance targets and/or guidelines.

FIG. 5 shows a model typical breath waveform of a person while sleeping.

The horizontal axis is time, and the vertical axis is respiratory flow rate. While the parameter values may vary, a typical breath may have the following approximate values: tidal volume, Vt, 0.5L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

4.7.2 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

4.7.3 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

PART NUMBERS 1000 patient
1100 bed partner
3000 patient interface
3100 seal-forming structure
3200 plenum chamber
3300 structure
3400 vent
3600 connection port
3700 forehead support
4000 RPT device
4010 external housing
4012 upper portion
4014 portion
4015 panel
4016 chassis
4018 handle
4020 pneumatic block
4100 pneumatic component
4110 air filter
4112 inlet air filter
4114 outlet air filter
4122 inlet muffler
4124 outlet muffler
4140 pressure generator
4142 blower
4142 controllable blower
4144 motor
4144 brushless DC motor
4170 air circuit
4180 supplemental oxygen
4200 electrical component
4202 PCBA
4210 electrical power supply
4220 input device
4230 central controller
4240 therapy device controller
4250 protection circuit
4260 memory
4270 transducer
4272 pressure sensor
4274 flow rate sensor
4280 data communication interface
4290 output device
5000 humidifier
5002 humidifier inlet
5004 humidifier outlet
5006 humidifier base
5110 reservoir
5120 conductive portion
5130 humidifier reservoir dock
5135 locking lever
5150 water level indicator
5240 heating element
6000 impeller
6000a first impeller
6000b second impeller
6002 hub
6004 hole
6006 inclined blade
6008 reverse inclined blade
6010a rotationally forward edge
6010b rotationally forward edge
6012a rotationally rearward edge
6012b rotationally rearward edge
6014 perimeter
6016 sector
6018 intermediate circumferential portion
6020 first flow path
6022 first face
6024 second flow path
6026 second face
6028 opening
6030 serration
6032 serration
6034 preferred direction of rotation
6036a leading edge
6036b leading edge
6038a trailing edge
6038b trailing edge
7000 mould 7002 mould half
7004 mould half
7006 direction of draw
8000 inlet
8002 outlet
8004 inlet cover
8006 outlet cover
8008 stator vane
8010 shield
8012 stator vane
8014 housing cover
8016 motor housing
8018 stator vane
8020 end face
8022 stator vane
8024 end bell
8026 acoustic cover
8028 motor cavity

The invention claimed is:

1. A respiratory pressure therapy device for generating a supply of air at positive pressure for the amelioration or treatment of a respiratory disorder, the respiratory pressure therapy device comprising:
a device outlet configured to connect to an air circuit to deliver the supply of air to a patient via a patient interface;
a controller configured to control the respiratory pressure therapy device to provide flow rates and pressures suitable for respiratory therapy; and
a pressure generator including an impeller for a centrifugal blower, a housing for the impeller that includes an inlet and an outlet, and an electric motor configured to rotate the impeller to generate the positive pressure, wherein the impeller comprises:
a hub defining an axis of rotation for the impeller;
a plurality of inclined blades, the plurality of inclined blades extending away from the hub, each inclined blade of the plurality of inclined blades including a leading edge and a trailing edge; and
a plurality of reverse inclined blades, the plurality of reverse inclined blades extending away from the hub, each reverse inclined blade of the plurality of reversed inclined blades including a leading edge and a trailing edge,
wherein each leading edge of the plurality of inclined blades and the plurality of reverse inclined blades being the most upstream edge of the impeller in use;
wherein each trailing edge of the plurality of inclined blades and the plurality of reverse inclined blades being the most downstream edge of the impeller in use;
wherein each of the plurality of inclined blades are joined to an adjacent inclined blade at least in part by a reverse inclined blade; and
wherein at least one of the plurality of inclined blades and/or at least one of the plurality of reverse inclined blades includes serrations on a respective trailing edge.

2. The respiratory pressure therapy device of claim 1, wherein each of the plurality of inclined blades includes serrations on a respective trailing edge.

3. The respiratory pressure therapy device of claim 1, wherein each of the plurality of reverse inclined blades includes serrations on a respective trailing edge.

4. The respiratory pressure therapy device of claim 1, wherein at least one of the plurality of inclined blades and/or at least one of the plurality of reverse inclined blades includes serrations on a respective leading edge.

5. The respiratory pressure therapy device of claim 4, wherein each of the plurality of inclined blades includes serrations on a respective leading edge.

6. The respiratory pressure therapy device of claim 1, wherein the leading edge of each inclined blade of the plurality of inclined blades is not parallel with respect to the trailing edge of each inclined blade of the plurality of inclined blades.

7. The respiratory pressure therapy device of claim 6, wherein each of the plurality of inclined blades and each of the plurality of reverse inclined blades provide a flow path in a direction from the hub towards an outer perimeter of the impeller, wherein the flow path extends along the leading edge of each inclined blade of the plurality of inclined blades, and wherein the flow path intersects the trailing edge of each inclined blade of the plurality of inclined blades.

8. The respiratory pressure therapy device of claim 6, further comprising an intermediate circumferential portion disposed between the hub and the trailing edges of the plurality of inclined blades and the trailing edges of the plurality of reverse inclined blades.

9. The respiratory pressure therapy device of claim 8, wherein the intermediate circumferential portion is disposed between the leading edges of the plurality of inclined blades and the trailing edges of the plurality of inclined blades.

10. The respiratory pressure therapy device of claim 1, wherein:
the plurality of inclined blades are inclined at a positive angle with the axis of rotation, the positive angle being neither parallel nor perpendicular;
the plurality of reverse inclined blades are inclined at a negative angle with the axis of rotation; and
the positive angle and the negative angle have the same absolute value.

11. The respiratory pressure therapy device of claim 1, wherein a blade tip of at least one of the plurality of inclined blades and the plurality of reverse inclined blades includes serrations.

12. The respiratory pressure therapy device of claim 1, wherein each of the plurality of inclined blades forms a substantially V-shaped cross-section with an adjacent reverse inclined blade.

13. The respiratory pressure therapy device of claim 1, wherein the impeller further includes a sector connecting an inclined blade of the plurality of inclined blades to an adjacent reverse inclined blade of the plurality of reverse inclined blades, wherein the sector is substantially perpendicular to the axis of rotation.

14. The respiratory pressure therapy device of claim 1, wherein the plurality of inclined blades and the plurality of reverse inclined blades define primary air passages on a first face of the impeller and secondary air passages on a second face of the impeller, and the inlet is open to and on the same side as the second face.

15. The respiratory pressure therapy device of claim 14, wherein the impeller comprises a plurality of openings in fluid communication with the inlet, the plurality of openings being configured to allow air to flow from the second face, toward the first face and radially outward through the primary passages.

16. The respiratory pressure therapy device of claim 1, wherein the plurality of inclined blades and the plurality of reverse inclined blades are formed without an undercut.

17. A respiratory pressure therapy device for generating a supply of air at positive pressure for the amelioration or treatment of a respiratory disorder, the respiratory pressure therapy device comprising:

a device outlet configured to connect to an air circuit to deliver the supply of air to a patient via a patient interface;

a controller configured to control the respiratory pressure therapy device to provide flow rates and pressures suitable for respiratory therapy; and a pressure generator including an impeller for a blower, a housing for the impeller that includes an inlet and an outlet, and an electric motor configured to rotate the impeller to generate the positive pressure, wherein the impeller comprises:

a hub defining an axis of rotation for the impeller;

a plurality of inclined blades, the plurality of inclined blades extending away from the hub, each inclined blade of the plurality of inclined blades including a leading edge and a trailing edge; and wherein each leading edge of the plurality of inclined blades being the most upstream edge of the impeller in use;

wherein each trailing edge of the plurality of inclined blades being the most downstream edge of the impeller in use;

wherein the leading edge of each inclined blade of the plurality of inclined blades is not parallel with respect to the trailing edge of each inclined blade of the plurality of inclined blades; and wherein at least one of the plurality of inclined blades includes serrations on a respective leading edge and on a respective trailing edge.

18. The respiratory pressure therapy device of claim 17, further comprising a plurality of reverse inclined blades, the plurality of reverse inclined blades extend away from the hub, each reverse inclined blade of the plurality of reversed inclined blades includes a leading edge and a trailing edge, wherein each leading edge of the plurality of reverse inclined blades is the most upstream edge of the impeller in use and each trailing edge is the most downstream edge of the impeller in use, wherein each of the plurality of inclined blades are joined to an adjacent inclined blade at least in part by a reverse inclined blade; and wherein at least one of the plurality of reverse inclined blades includes serrations on a respective trailing edge.

19. The respiratory pressure therapy device of claim 18, wherein each of the plurality of inclined blades forms a substantially V-shaped cross-section with an adjacent reverse inclined blade.

20. The respiratory pressure therapy device of claim 17, wherein each inclined blade of the plurality of inclined blades includes serrations on a respective leading edge and on a respective trailing edge.

21. The respiratory pressure therapy device of claim 17, further comprising an intermediate circumferential portion disposed between the hub and the trailing edges of the plurality of inclined blades.

22. The respiratory pressure therapy device of claim 21, wherein the intermediate circumferential portion is disposed between the leading edges of the plurality of inclined blades and the trailing edges of the plurality of inclined blades.

23. The respiratory pressure therapy device of claim 22, wherein the serrations on the respective leading edge of the at least one of the plurality of inclined blades extends entirely between the intermediate circumferential portion and the hub.

24. The respiratory pressure therapy device of claim 17, wherein the plurality of inclined blades are inclined at a positive angle with the axis of rotation, the positive angle being neither parallel nor perpendicular.

25. The respiratory pressure therapy device of claim 17, wherein a blade tip of at least one of the plurality of inclined blades includes serrations.

26. The respiratory pressure therapy device of claim 17, wherein each of the plurality of inclined blades at least partially forms a flow path in a direction from the hub towards an outer perimeter of the impeller, wherein the flow path extends along the leading edge of each inclined blade of the plurality of inclined blades, and wherein the flow path intersects the trailing edge of each inclined blade of the plurality of inclined blades.

27. The respiratory pressure therapy device of claim 18, wherein the plurality of inclined blades and the plurality of reverse inclined blades are formed without an undercut.

28. The respiratory pressure therapy device of claim 1, wherein the impeller comprises an injection moulded construction.

29. The respiratory pressure therapy device of claim 1, wherein the impeller comprises a one-piece unitary structure.

30. The respiratory pressure therapy device of claim 17, wherein the impeller comprises an injection moulded construction.

31. The respiratory pressure therapy device of claim 17, wherein the impeller comprises a one-piece unitary structure.

* * * * *